US012759970B2

(12) United States Patent
Dhawan et al.

(10) Patent No.: US 12,759,970 B2
(45) Date of Patent: Oct. 13, 2026

(54) POLYHYDROXY MULTI-IONIC COMPOUNDS AND METHODS OF MAKING AND USE THEREOF

(71) Applicant: ECOLAB USA INC., Saint Paul, MN (US)

(72) Inventors: Ashish Dhawan, Saint Paul, MN (US); Carter M. Silvernail, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 627 days.

(21) Appl. No.: 18/304,567

(22) Filed: Apr. 21, 2023

(65) Prior Publication Data

US 2023/0339849 A1 Oct. 26, 2023

Related U.S. Application Data

(60) Provisional application No. 63/363,428, filed on Apr. 22, 2022.

(51) Int. Cl.
*C07C 233/36* (2006.01)

(52) U.S. Cl.
CPC .................................. *C07C 233/36* (2013.01)

(58) Field of Classification Search
None
See application file for complete search history.

(56) References Cited

U.S. PATENT DOCUMENTS

| | | |
|---|---|---|
| 2,195,974 A | 4/1940 | Reppe et al. |
| 3,077,487 A | 2/1963 | Ramsey et al. |
| 3,793,194 A | 2/1974 | Zecher |
| 3,794,586 A | 2/1974 | Kimura et al. |
| 4,075,136 A | 2/1978 | Schaper |
| 4,166,894 A | 9/1979 | Schaper |
| 4,195,138 A | 3/1980 | Ward |
| 4,246,030 A | 1/1981 | Lipinski |
| 4,259,217 A | 3/1981 | Murphy |
| 4,355,071 A | 10/1982 | Chang |
| 4,650,000 A | 3/1987 | Andreasson et al. |

(Continued)

FOREIGN PATENT DOCUMENTS

| | | |
|---|---|---|
| CN | 1340031 A | 3/2002 |
| CN | 101972612 A | 2/2011 |

(Continued)

OTHER PUBLICATIONS

Song et al. (Biomacromolecules, 2020, 21(12), 5345-5357) (Year: 2020).*

(Continued)

*Primary Examiner* — Renee Claytor
*Assistant Examiner* — Jennifer C Sawyer
(74) *Attorney, Agent, or Firm* — McKee, Voorhees & Sease, PLC

(57) ABSTRACT

Polyhydroxy multiple charged ionic compounds that are the reaction product from either a single amidation and aza-Michael addition reaction or a two-step process of synthesizing a gluconamide intermediate and thereafter undergoing an aza-Michael Addition reaction between the gluconamide intermediate and an ionic monomer are disclosed. Methods of making the multiple charged ionic compounds, and uses thereof are also disclosed.

20 Claims, 6 Drawing Sheets

(56) References Cited

U.S. PATENT DOCUMENTS

| | | | |
|---|---|---|---|
| 4,692,315 | A | 9/1987 | Greaves et al. |
| 4,705,665 | A | 11/1987 | Malik |
| 4,784,797 | A | 11/1988 | Treybig et al. |
| 4,798,675 | A | 1/1989 | Lipinski et al. |
| 5,019,343 | A | 5/1991 | Wa et al. |
| 5,053,150 | A | 10/1991 | Emert et al. |
| 5,192,798 | A | 3/1993 | Aiken et al. |
| 5,399,746 | A | 3/1995 | Steiger et al. |
| 5,462,714 | A | 10/1995 | Talwalker et al. |
| 5,614,616 | A | 3/1997 | Buysch et al. |
| 5,670,464 | A | 9/1997 | Kita et al. |
| 5,738,795 | A | 4/1998 | Chen |
| 5,788,866 | A | 8/1998 | Fong et al. |
| 6,004,466 | A | 12/1999 | Derian et al. |
| 6,054,054 | A | 4/2000 | Robertson et al. |
| 6,080,323 | A | 6/2000 | Yu et al. |
| 6,090,754 | A | 7/2000 | Chan et al. |
| 6,156,222 | A | 12/2000 | Jennings et al. |
| 6,238,621 | B1 | 5/2001 | Kalota et al. |
| 6,503,880 | B1 | 1/2003 | Skold et al. |
| 6,627,612 | B1 | 9/2003 | O'Lenick, Jr. et al. |
| 6,797,785 | B1 | 9/2004 | Hund et al. |
| 6,881,710 | B1 | 4/2005 | O'Lenick, Jr. et al. |
| 6,984,340 | B1 | 1/2006 | Brady et al. |
| 7,052,614 | B2 | 5/2006 | Barak |
| 7,084,129 | B1 | 8/2006 | Smith et al. |
| 7,345,015 | B1 | 3/2008 | Kong et al. |
| 7,375,064 | B1 | 5/2008 | O'Lenick, Jr. |
| 7,507,399 | B1 | 3/2009 | O'Lenick, Jr. |
| 7,604,978 | B2 | 10/2009 | Eldridge |
| 8,324,264 | B1 | 12/2012 | Eldridge et al. |
| 8,933,055 | B2 | 1/2015 | Pedersen et al. |
| 9,388,361 | B2 | 7/2016 | Terada et al. |
| 9,956,153 | B2 | 5/2018 | Emiru et al. |
| 10,850,999 | B2 | 12/2020 | DiMascio et al. |
| 10,945,431 | B2 | 3/2021 | Karandikar et al. |
| 11,058,111 | B2 | 7/2021 | Dhawan et al. |
| 11,084,974 | B2 | 8/2021 | Dhawan et al. |
| 11,236,040 | B2 | 2/2022 | Dhawan et al. |
| 11,261,113 | B2 | 3/2022 | Dhawan et al. |
| 11,292,734 | B2 | 4/2022 | Dhawan et al. |
| 11,685,709 | B2 | 6/2023 | Dhawan et al. |
| 11,702,586 | B2 | 7/2023 | Dhawan et al. |
| 11,926,543 | B2 | 3/2024 | Dhawan et al. |
| 2001/0044393 | A1 | 11/2001 | Peterson, Jr. et al. |
| 2002/0104349 | A1 | 8/2002 | Richter et al. |
| 2002/0155978 | A1 | 10/2002 | Man et al. |
| 2003/0121532 | A1 | 7/2003 | Coughlin et al. |
| 2004/0009139 | A1 | 1/2004 | Oldenhove |
| 2005/0061197 | A1 | 3/2005 | Nalepa |
| 2005/0215461 | A1 | 9/2005 | Gluck et al. |
| 2005/0261484 | A1 | 11/2005 | Pascaly et al. |
| 2006/0008496 | A1 | 1/2006 | Kulkarni et al. |
| 2006/0231505 | A1 | 10/2006 | Mayer et al. |
| 2006/0289164 | A1 | 12/2006 | Smith et al. |
| 2006/0289359 | A1 | 12/2006 | Manek et al. |
| 2008/0152567 | A1 | 6/2008 | Killough |
| 2009/0236571 | A1 | 9/2009 | Cohen |
| 2010/0004316 | A1 | 1/2010 | Lu et al. |
| 2010/0029530 | A1 | 2/2010 | Whiteley |
| 2010/0305014 | A1 | 12/2010 | Miralles et al. |
| 2010/0331234 | A1 | 12/2010 | Mahon et al. |
| 2011/0112007 | A1 | 5/2011 | Hodge et al. |
| 2011/0296746 | A1 | 12/2011 | Hernandez Altamirano et al. |
| 2012/0053111 | A1 | 3/2012 | Hodge et al. |
| 2012/0070341 | A1 | 3/2012 | Eder et al. |
| 2012/0071438 | A1 | 3/2012 | Pedersen et al. |
| 2012/0115962 | A1 | 5/2012 | Lee et al. |
| 2012/0258157 | A1 | 10/2012 | Koltzenburg et al. |
| 2013/0228095 | A1 | 9/2013 | Miles et al. |
| 2013/0266669 | A1 | 10/2013 | Jiang et al. |
| 2014/0091262 | A1 | 4/2014 | Webber et al. |
| 2014/0124454 | A1 | 5/2014 | Nichols et al. |
| 2014/0224733 | A1 | 8/2014 | Osness et al. |
| 2014/0339462 | A1 | 11/2014 | Berte et al. |
| 2015/0203738 | A1 | 7/2015 | Witham et al. |
| 2015/0272124 | A1 | 10/2015 | Pedersen et al. |
| 2015/0290100 | A1 | 10/2015 | Eder et al. |
| 2016/0010035 | A1 | 1/2016 | Liu et al. |
| 2016/0030315 | A1 | 2/2016 | Emiru et al. |
| 2016/0130494 | A1 | 5/2016 | Paid et al. |
| 2016/0145610 | A1 | 5/2016 | Lu et al. |
| 2016/0186040 | A1 | 6/2016 | Gill |
| 2016/0215198 | A1 | 7/2016 | Qu et al. |
| 2016/0262999 | A1 | 9/2016 | Pedersen et al. |
| 2016/0264734 | A1 | 9/2016 | Boday et al. |
| 2016/0264744 | A1 | 9/2016 | Boday et al. |
| 2017/0029691 | A1 | 2/2017 | Faust, Jr. et al. |
| 2017/0121560 | A1 | 5/2017 | Dockery et al. |
| 2017/0130340 | A1 | 5/2017 | Kalakodimi et al. |
| 2017/0137634 | A1 | 5/2017 | Balasubramanian et al. |
| 2017/0233643 | A1 | 8/2017 | Agashe et al. |
| 2017/0247798 | A1 | 8/2017 | Moloney |
| 2017/0349543 | A1 | 12/2017 | Siegwart et al. |
| 2017/0360040 | A1 | 12/2017 | Kost et al. |
| 2018/0007895 | A1 | 1/2018 | Karandikar et al. |
| 2018/0066211 | A1 | 3/2018 | Pickering et al. |
| 2018/0105629 | A1 | 4/2018 | Tada et al. |
| 2018/0118999 | A1 | 5/2018 | Hikem et al. |
| 2018/0163020 | A1 | 6/2018 | Zong et al. |
| 2018/0192643 | A1 | 7/2018 | Fast et al. |
| 2019/0062187 | A1 | 2/2019 | Dhawan et al. |
| 2019/0223434 | A1 | 7/2019 | Balasubramanian et al. |
| 2019/0224627 | A1 | 7/2019 | Glanz et al. |
| 2020/0068885 | A1 | 3/2020 | Dhawan et al. |
| 2020/0071205 | A1 | 3/2020 | Dhawan et al. |
| 2020/0071261 | A1 | 3/2020 | Dhawan et al. |
| 2020/0071265 | A1 | 3/2020 | Dhawan et al. |
| 2020/0071602 | A1 | 3/2020 | Dhawan et al. |
| 2020/0332423 | A1 | 10/2020 | Dhawan et al. |
| 2022/0163891 | A1 | 5/2022 | Eum et al. |

FOREIGN PATENT DOCUMENTS

| | | | |
|---|---|---|---|
| CN | 102504247 | A | 6/2012 |
| CN | 102675535 | A | 9/2012 |
| CN | 103118655 | A | 5/2013 |
| CN | 103288672 | A | 9/2013 |
| CN | 103483539 | A | 1/2014 |
| CN | 104130335 | A | 11/2014 |
| CN | 104130351 | A | 11/2014 |
| CN | 104744709 | A | 7/2015 |
| CN | 105076201 | A | 11/2015 |
| CN | 105523956 | A | 4/2016 |
| CN | 105884640 | A | 8/2016 |
| CN | 106172434 | A | 12/2016 |
| CN | 106423269 | A | 2/2017 |
| CN | 106423284 | A | 2/2017 |
| CN | 106634929 | A | 5/2017 |
| CN | 106750235 | A | 5/2017 |
| CN | 106946743 | A | 7/2017 |
| CN | 107440935 | A | 12/2017 |
| CN | 108033895 | A | 5/2018 |
| CN | 108048249 | A | 5/2018 |
| CN | 108938662 | A | 12/2018 |
| CN | 111315718 | A | 6/2020 |
| EP | 0185970 | A1 | 7/1986 |
| EP | 0291590 | A1 | 11/1988 |
| EP | 296441 | A2 | 12/1988 |
| EP | 0745648 | A2 | 12/1996 |
| EP | 0955327 | A2 | 11/1999 |
| EP | 1690960 | A2 | 8/2006 |
| EP | 2333135 | A1 | 6/2011 |
| GB | 847321 | A | 9/1960 |
| GB | 1550420 | A | 8/1979 |
| JP | S4431461 | A | 12/1969 |
| JP | S57185322 | A | 11/1982 |
| JP | S58105908 | A | 6/1983 |
| JP | S6139937 | B2 | 9/1986 |
| JP | S6259602 | A | 3/1987 |
| JP | H06116351 | A2 | 4/1994 |
| JP | H06116898 | A | 4/1994 |
| JP | H0913066 | A | 1/1997 |
| JP | 2001187751 | A | 7/2001 |

(56) References Cited

FOREIGN PATENT DOCUMENTS

| | | | |
|---|---|---|---|
| JP | 2007054710 | A | 3/2007 |
| JP | 2007077082 | A | 3/2007 |
| JP | 2007256445 | A | 10/2007 |
| JP | 2012136504 | A | 7/2012 |
| JP | 2014009177 | A | 1/2014 |
| JP | 2014093768 | A | 5/2014 |
| JP | 2014221859 | A | 11/2014 |
| JP | 2015101552 | A | 6/2015 |
| JP | 2015189857 | A | 11/2015 |
| JP | 2017525798 | A | 9/2017 |
| NO | 2006092736 | A2 | 9/2006 |
| WO | 3035797 | A1 | 5/2003 |
| WO | 2004046211 | A1 | 6/2004 |
| WO | 2004056843 | A2 | 7/2004 |
| WO | 2008079729 | A1 | 7/2008 |
| WO | 2009153209 | A1 | 12/2009 |
| WO | 2012083497 | A1 | 6/2012 |
| WO | 2013087287 | A1 | 6/2013 |
| WO | 2014079621 | A1 | 5/2014 |
| WO | 2015084304 | A1 | 6/2015 |
| WO | 2016205513 | A1 | 12/2016 |
| WO | 2017003639 | A2 | 1/2017 |
| WO | 2017201076 | A1 | 11/2017 |
| WO | 2018112548 | A1 | 6/2018 |
| WO | 2019046409 | A1 | 3/2019 |

OTHER PUBLICATIONS

"Azamethonium", http://pubchem.ncbi.nlm.nih.gov/compound/9383, last modified Oct. 6, 2018 and accessed by Applicant Oct. 11, 2018.

Bi et al., "Dendrimer-Based Demulsifiers for Polymer Flooding Oil-in-Water Emulsions", Energy Fuels, vol. 31. No. 5, pp. 5395-5401, Apr. 20, 2017.

Bosica et al., "Aza-Michael Mono-addition Using Acidic Alumina under Solventless Conditions", Molecules, vol. 21, 11 pages, Jun. 22, 2016.

Brycki et al., "The biodegradalion of monomeric and dimeric alkylammonium surfactants", Journal of Hazardous Materials, vol. 280, pp. 797-815, Aug. 6, 2014.

Ecolab USA Inc., in connection with PCT/US2019/048451 filed Aug. 28, 2019, "The International Search Report and the Written Opinion of the International Searching Authority, or the Declaration", 22 pages, mailed Jan. 29, 2020.

Fan et al., "Synthesis and Aggregation Behavior of a Hexameric Quaternary Ammonium Surfactant", Langmuir, vol. 27, pp. 10570-10579, Jul. 28, 2011.

Gan et al., "Sugar-Based Ester Quaternary Ammonium Compounds and Their Surfactant Properties", Journal of Surfactants and Detergents, vol. 17, Issue 3, pp. 465-470, Jan. 18, 2014.

International Preliminary Examining Authority in connection with PCT/US2019/048451 filed Aug. 28, 2019, "The International Preliminary Report of Patentability", 29 pages, mailed Sep. 7, 2020.

Kawakami et al., "Antibacterial Activity of Radial Compounds with Peripheral Quaternary Ammonium Units", Transactions of the Materials Research Society of Japan, vol. 35[4], pp. 885-887, 2010.

Database Caplus [Online] 1-12, 14, INV. 15 C07C237/10 Jan. 1, 2014 (Jan. 1, 2014), 3v Sigma S.P.A et al: "Stilbene optical brighteners for paper and detergent compositions —US 20140339462 A1", XP093289617, Database Accession No. 2014:1943408 * abstract *.

Extended European Search Report in EP24221857.6, mailed Mar. 21, 2025, 9 pages.

Kramer et al., "Dendritic polyamines: simple access to new materials with defined treelike structures for application in nonviral gene delivery", Chembiochem, vol. 5(8), pp. 1081-1087, Aug. 6, 2004.

Labade et al., "Cesium fluoride catalyzed Aza-Michael addition reaction in aqueous media", Monatsh Chem., vol. 142, pp. 1055-1059, Jul. 19, 2011.

Mann et al., "Acetal-initiated cyclization of allylsilanes to highly functionalized piperidine derivatives", Tetrahedron Letters, vol. 29 (26), pp. 3247-3250, 1988.

Miller et al., "Non-viral CRISPR/Cas gene editing in vitro and in vivo enabled by synthetic nanoparticle co-delivery of Cas9 mRNA and sgRNA", Angew Chem Int Ed Engl., vol. 56(4), pp. 1059-1063, Jan. 19, 2017.

Negm et al., "Synthesis, Characterization and Biological Activity of Sugar-Based Gemini Cationic Amphiphiles", Journal of Surfactants and Detergents, vol. 11, Issue 3, pp. 215-221, Jun. 13, 2008.

Ning et al., "Synthesis and characterization of a novel non-polyether demulsifier", Chemical Engineer, 3 pages, 2013.

Poly Suga Quat, Colonial Chemical, Inc., 2022, 4 pages.

Registry 1025555-14-9, accessed online on Aug. 14, 2021, 1 page, registered Jun. 5, 2008.

Registry 1025555-15-0, accessed online on Aug. 14, 2021, 1 page, registered Jun. 5, 2008.

Registry 1346596-75-5, accessed online on Aug. 14, 2021, 1 page, registered Nov. 30, 2011.

Registry 1346596-76-6, accessed online on Aug. 14, 2021, 1 page, registered Nov. 30, 2011.

Registry 1346596-77-7, accessed online on Aug. 14, 2021, 1 page, registered Nov. 30, 2011.

Registry 1801234-01-4, accessed online on Aug. 14, 2021, 1 page, registered Aug. 3, 2015.

Registry 1801234-02-5, accessed online on Aug. 14, 2021, 1 page, registered Aug. 3, 2015.

Registry 2000293-27-4, accessed online on Aug. 14, 2021, 1 page, registered Sep. 26, 2016.

Registry 2001056-21-7, accessed online on Aug. 14, 2021, 1 page, registered Sep. 27, 2016.

Registry 790647-93-7, accessed online on Aug. 14, 2021, 1 page, registered Nov. 30, 2004.

Registry 881538-24-5, accessed online on Aug. 14, 2021, 1 page, registered Apr. 21, 2006.

Registry 881538-25-6, accessed online on Aug. 14, 2021, 1 page, registered Apr. 21, 2006.

Registry 881538-26-7, accessed online on Aug. 14, 2021, 1 page, registered Apr. 21, 2006.

Registry 930395-29-2, accessed online on Aug. 14, 2021, 1 page, registered Apr. 17, 2007.

Registry 951236-20-7, accessed online on Aug. 14, 2021, 1 page, registered Oct. 23, 2007.

Registry 951236-22-9, accessed online on Aug. 14, 2021, 1 page, registered Oct. 23, 2007.

Registry 951236-51-4, accessed online on Aug. 14, 2021, 1 page, registered Oct. 23, 2007.

Somerscales, Euan F.C., "Fundamentals of Corrosion Fouling", Experimental Thermal and Fluid Science, vol. 14, pp. 335-355, 1997.

Tan et al., "The use of quaternised chitosan-loaded PMMA to inhibit biofilm formation and downregulate the virulence-associated gene expression of antibiotic-resistant *Staphylococcus*", Biomaterials, vol. 33, Issue 2, pp. 365-377, Jan. 2012.

Twyman, Lance J., "Post synthetic modification of the hydrophobic interior of a water-soluble dendrimer", Tetrahedron Letters, vol. 41 (35), pp. 6875-6878, 2000.

Wang et al., "A novel environment-sensitive biodegradable polydisulfide with protonatable pendants for nucleic acid delivery", Journal of Controlled Release, vol. 120, pp. 250-258, May 11, 2007.

Zaky, Mohamad, "Biocidal Activities of Cationic Surface Active Starch and Its Transition Metal Complexes Against Different Bacterial Strains", Journal of Surfactants and Detergents, vol. 13, Issue 3, pp. 255-260, Jul. 2010.

Zhang et al., "Controllable Self-Assembly of Amphiphilic Dendrimers on a Silica Surface: The Effect of Molecular Topological Structure and Salinity", Journal of Physical Chemistry, vol. 8, pp. 10990-10999, Oct. 5, 2016.

Zhang et al., "PAMAM-Based Dendrimers with Different Alkyl Chains Self-Assemble on Silica Surfaces: Controllable Layer Structure and Molecular Aggregation", J. Phys. Chem. B, vol. 122, pp. 6648-6655, Jun. 13, 2018.

(56) References Cited

OTHER PUBLICATIONS

Zhang et al., “Supporting Information”, Beijing National Laboratory for Molecular Sciences, published with Controllable Self-Assembly of Amphiphilic Dendrimers on a Silica Surface: Effect of Molecular Topological Structure and Salinity, 4 pages Oct. 5, 2016.
Zhi et al., “Self-aggregation and antimicrobial activity of saccharide-cationic surfactants”, Colloids and Surfaces A: Physicochemical and Engineering Aspects, vol. 456, pp. 231-237, Aug. 2014.
Zhou et al., “Cooperative binding and self-assembling behavior of cationic low molecular-weight dendrons with RNA molecules”, Organic & Biomolecular Chemistry, vol. 4, pp. 581-585, 2006.
Zielinski et al., “Synthesis of new quaternary ammonium salts for organophilization of fillers for polymeric nanocomposites”, www.miesiecznikchemik.pl, 2007.
Extended European Search Report in EP25222574.3, mailed Feb. 12, 2026, 8 pages.
Burton et al. “Epoxy formulations using Jeffamine® polyetheramines.” Huntsman Corp 1.1 (2005): 1-103.
CAS Scifinder, Substances search results for: us4166894, Task History [online], CAS SciFinder®, 2026 [retrieved on Mar. 5, 2026], 7 pages.
Database PubChem: 162071, “Ethanaminium, N,N,N-trimethyl-2-[(1-oxo-2-propen-1-yl)oxy]-, chloride (1:1).” PubChem CID: 162071, Aug. 8, 2005. Retrieved from the Internet: <URL: https://pubchem.ncbi.nlm.nih.gov/compound/162071>, 5 pages.
Database PubChem: 6435904, “N-Oleyl-1,3-propanediamine.” PubChem CID: 6435904, Apr. 28, 2006. Retrieved from the Internet: <URL: https://pubchem.ncbi.nlm.nih.gov/compound/N-Oleyl-1_3-propanediamine>, 3 pages.
Database PubChem: 69332, “4-Amino-N-methylaniline.” PubChem CID: 69332, Mar. 26, 2005. Retrieved from the Internet: <URL: https://pubchem.ncbi.nlm.nih.gov/compound/4-Amino-N-methylaniline>, 1 page.
Peng et al. “Synthesis and application of polyoxyethylene-grafted cationic polyamidoamine dendrimers as retention aids.” Journal of applied polymer science 106.5 (2007): 3468-3473.

* cited by examiner (I)

(II)

(IIIb)

or (IIIa)

1

2

(IIIa)

3

4

5

(IIIb)

6

7

(VI)

Branched Polyethyleneimine (I)

(IV)

(VII)

POLYHYDROXY MULTI-IONIC COMPOUNDS AND METHODS OF MAKING AND USE THEREOF

CROSS REFERENCE TO RELATED APPLICATIONS

This application claims priority under 35 U.S.C. § 119 to provisional patent application U.S. Ser. No. 63/363,428, filed Apr. 22, 2022. The provisional patent application is herein incorporated by reference in its entirety, including without limitation, the specification, claims, and abstract, as well as any figures, tables, appendices, or drawings thereof.

TECHNICAL FIELD

The disclosure relates generally to the field of multiple charged ionic compounds, namely polyhydroxy multi-ionic compounds, methods of making the same, and use thereof. The present disclosure also relates generally to the field of using the ionic compounds in a reverse emulsion breaker composition, in a drag reducer composition, in a water clarifier composition, in a clay stabilizer composition, in a biofilm inhibitor composition, and in various formulations as adjuvants including rheology modifiers, viscosity reducers composition, and/or emulsion inverters. These compositions and formulation adjuvants have applications in various water treatment, oil and gas operations, and/or cleaning products. In particular, the present disclosure relates to a novel class of multiple charged ionic compounds that are derived from either a single amidation and aza-Michael addition reaction or a two-step process including synthesis of a gluconoamide intermediate and thereafter an aza-Michael Addition reaction between the gluconoamide intermediate and an ionic monomer. Methods of making the polyhydroxy multiple charged ionic compounds, and uses thereof are also disclosed. In embodiments, the disclosed polyhydroxy multiple charged ionic compounds (or their salts) have at least two or three charges within each molecule.

BACKGROUND

There are various water treatment, oil and gas operations, and formulation applications that require novel and improved ionic compounds, namely cationic or anionic compounds, including polyhydroxy multi-ionic compounds. The characteristics of ionic compounds have various applications of use, such as those employing quaternary ammonium compounds, useful as disinfectants, surfactants, and the like. Similarly, the characteristics of polyhydroxyl compounds, or polyols, are useful in various water treatment and other oil and gas applications, such as formulation adjuvants, gellant, thickeners, rheology modifiers and components of many cleaning products. There is an ongoing need for identification of novel compounds with properties to differentiate from or offer synergistic benefits in these various application areas.

For example, the separation of the oil and solids from water is needed to comply with the oil sales specifications and to provide acceptable specifications before the water can be disposed or re-used. However, desirable oil/hydrocarbon and water separation for an oil-in-water emulsion or complex emulsion can be difficult by physical processes alone, due to the nature of emulsion. In such circumstances, demulsifying coagulants and flocculants, e.g., a reverse emulsion breaker (REB) can be used to break the emulsion and hasten agglomeration of the oil particles. Inorganic coagulants alone or in combination with organic polyelectrolytes have been used in de-emulsification of a produced fluid in oil and gas operations.

Quaternary ammonium compounds have been used for many years as REB agents. Quaternary ammonium compounds belong to an important subcategory of surfactants because they contain unique properties. A main distinction between quaternary ammonium compounds from other surfactants is their unique structure. Quaternary ammonium compounds consist mainly of two moieties, a hydrophobic group, e.g., long alkyl group, and a quaternary ammonium salt group. The unique positive charge of the ammonium plays a key role, e.g., electrostatic interactions, between the surfactant and surface or charge neutralization on surfaces of emulsion droplets. However, the quaternary ammonium compounds used for such purpose are often bis quaternary species or species quaternized with benzyl chloride that are known to be very hazardous. In additional, governmental regulations exist to release any water containing single quaternary compounds into environment. Therefore, there is a continuing need for ionic compounds that can replace quaternary ammonium compounds for enhanced performance and safety as REBs.

There are various other applications for REBs and emulsion inverters. Oil-in-water and water-in-oil-in-water emulsions can occur in many industrial systems. For example, a produced fluid containing emulsified oil, e.g., a reverse emulsion or a complex emulsion containing oil-in-water emulsion and dispersed solids, is common in oil and gas operation.

There are still other applications where novel cationic and anionic charged compounds can be employed. It is therefore an object of this disclosure to provide polyhydroxy multi-ionic compounds, methods of making the same, and compositions employing the ionic compounds.

It is a further objective of the disclosure to develop methods of making the novel ionic compounds having multiple hydroxy groups and ionic groups on the same molecule core, and providing methods of making that are efficient and effective.

It is a further objective of the disclosure to use the novel compounds in an article, product, and/or composition.

It is an objective to develop novel REB agents with improved properties having improved oil/hydrocarbon and water separation properties.

It is a still further objective to develop novel water clarifiers, clay stabilizers, biofilm inhibitors, rheology modifiers, drag reducers, viscosity reducers, and the like having at least two or three positive or negative charges within each molecule to provide the combined properties of ionic compounds and polyhydroxy compounds.

Other objects, embodiments and advantages of this invention will be apparent to one skilled in the art in view of the following disclosure, the drawings, and the appended claims.

BRIEF SUMMARY

Disclosed herein are novel polyhydroxy ionic compounds, methods of making the disclosed compounds, and articles, products, or compositions comprising the disclosed compounds. More particularly, the disclosed herein are the polyhydroxy multiple charged ionic compounds comprising multiple positive or negative charges within single molecules of various molecule sizes and derived from sugar lactones and water-soluble polyamines to synthesize a gluconoamide intermediate that is then reacted with an ionic monomer through an aza-Michael addition reaction. It is a primary object, feature, and/or advantage of the present invention to synthesize compounds with multiple hydroxy groups and multiple ionic groups on the same molecule core. Beneficially, the multi-ionic compounds have improved properties of both ionic compounds (e.g., quaternary ammonium compounds) and polyhydroxyl compounds (e.g., polyols) in a single polyhydroxy multi-ionic compound.

According to aspects of the present disclosure, polyhydroxy multi-ionic compounds are disclosed as having the structure of formula V or VII:

(V)

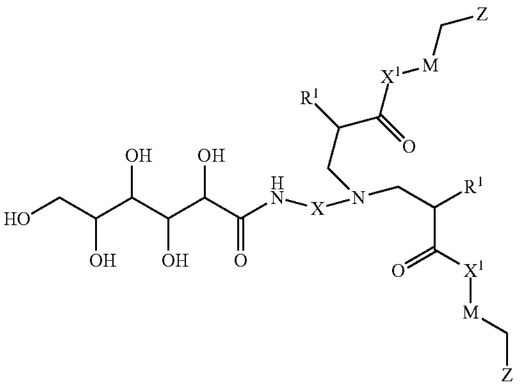

or (VII)

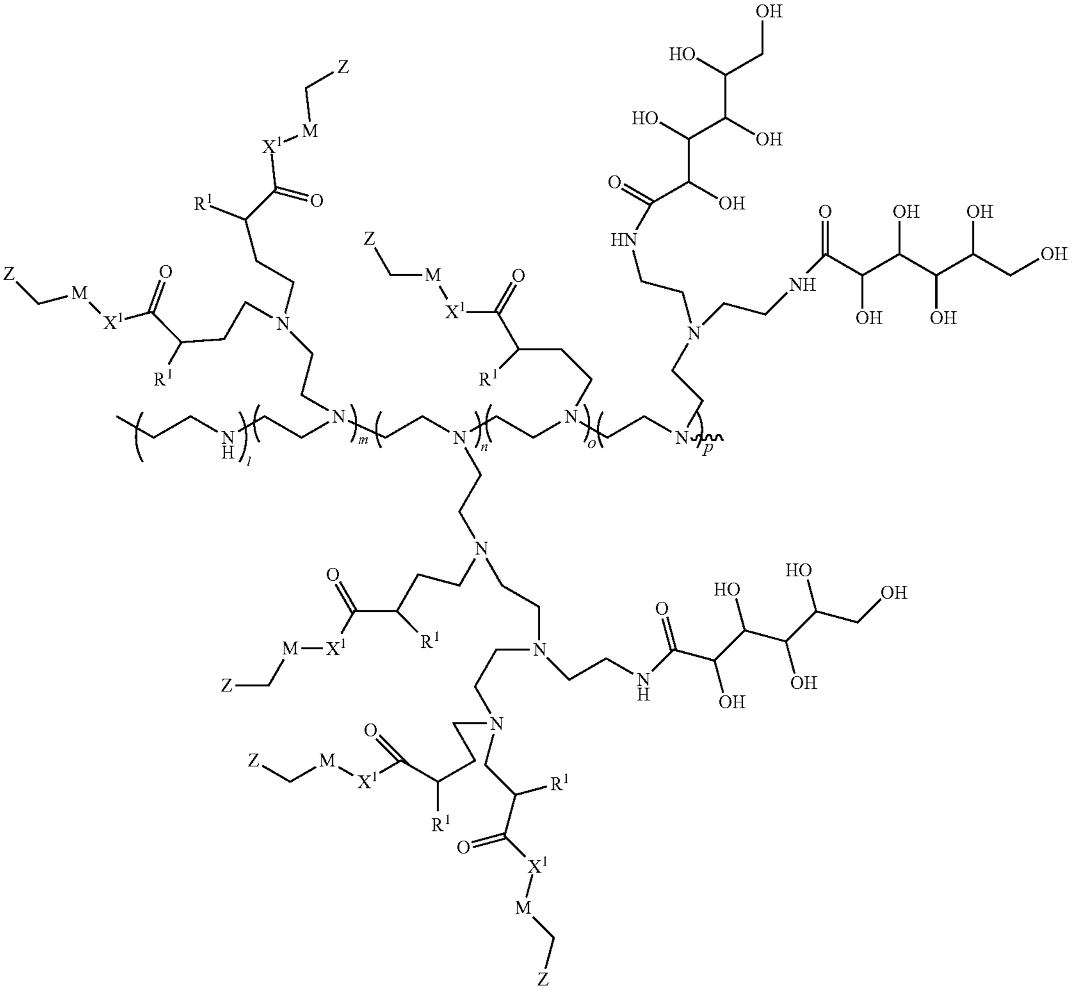

wherein:

l, m, n, o, and p are independently an integer of 0-1000, and wherein at least one of 1, m, n, o, and/or p is an integer of 1-1000;

X is $-(CH_2)_{m1}-$, $-(Ar)-$, $-(CH_2Ar)_{n1}-$, $-((CH_2)_{o1}Ar(CH_2)_{o1})_{p1}-$, $-((CH_2)_qNH(CH_2)_q)_r-$, or $-(CH_2NDCH_2)_s-$, wherein D is H,

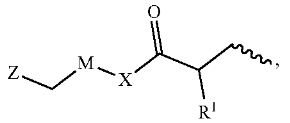

or

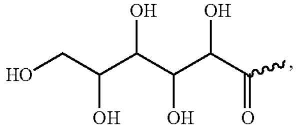

wherein $m_1$, $n_1$, $o_1$, and q are independently an integer from 0 to 10 and $p_1$, r, and s are independently an integer from 1 to 100;

X is NH or O;

$R^1$ is H, $CH_3$, or an unsubstituted, linear or branched C2-C10 alkyl group;

M is absent or an unsubstituted, linear C1-C30 alkylene group;

Z is $-NR^3R^4R^5(+)\ Y(-)$, $-COOH$, $-SO_3H$, $-PO_3H$, or a salt thereof; and $R^3$, $R^4$, and $R^5$ are independently C1-C10 alkyl group or benzyl group.

According to additional aspects of the present disclosure, polyhydroxy multi-ionic compounds comprise: a reaction product obtained by either: (a) reacting a sugar lactone with a polyamine to form a sugar amide intermediate through amidation; and thereafter undergoing an aza-Michael addition reaction between the sugar amide intermediate and a cationic/anionic monomer to form the polyhydroxy multi-ionic compound as described having the structure of formula V or VII; or (b) simultaneously reacting a polyamine with a sugar lactone and a cationic/anionic monomer to form the polyhydroxy multi-ionic compound as described having the structure of formula V or VII.

According to additional aspects of the disclosure, methods of synthesizing a polyhydroxy multi-ionic compound are also disclosed.

According to some other aspects of the present disclosure, methods of breaking an emulsion of water and oil comprise introducing an effective amount of an emulsion breaker composition into contact with the emulsion to destabilize the emulsion, wherein the emulsion breaker composition comprises a polyhydroxy multi-ionic compound as described having the structure of formula V or VII.

According to some other aspects of the present disclosure, methods of clarifying a water source comprise introducing an effective amount of an water clarification composition into contact with the water source, wherein the water clarification composition comprises a polyhydroxy multi-ionic compound as described having the structure of formula V or VII.

According to some other aspects of the present disclosure, methods of stabilizing swellable clays and/or reducing formation of sludge in a subterranean formation comprise introducing an effective amount of a clay treatment composition into a subterranean formation with a fluid, wherein the clay treatment composition comprises a polyhydroxy multi-ionic compound as described having the structure of formula V or VII.

According to some other aspects of the present disclosure, methods of inverting an emulsion of water and oil comprise introducing an effective amount of an emulsion inverter composition into contact with the emulsion to destabilize the emulsion, wherein the emulsion inverter composition comprises a polyhydroxy multi-ionic compound as described having the structure of formula V or VII.

According to some other aspects of the present disclosure, methods of inhibiting bio-film comprise introducing an effective amount of a bio-film inhibitor, wherein the bio-film inhibitor comprises a polyhydroxy multi-ionic compound as described having the structure of formula V or VII.

According to some other aspects of the present disclosure, methods of reducing drag in a fluid comprise introducing an effective amount of a drag reducer composition comprising a polyhydroxy multi-ionic compound as described having the structure of formula V or VII.

According to some other aspects of the present disclosure, methods of viscosity and/or rheology modification comprise introducing an effective amount of viscosity and/or rheology modifier composition, wherein the viscosity and/or rheology modifier composition comprises a polyhydroxy multi-ionic compound as described having the structure of formula V or VII.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

Figure 1A:
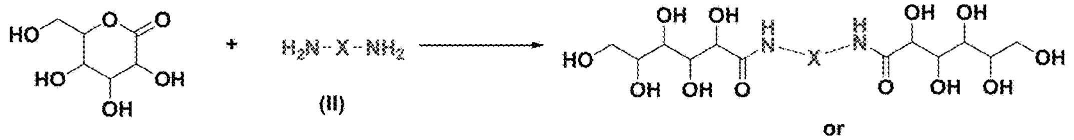
FIG. 1A shows an exemplary synthesis of a gluconoamide intermediate.
Figure 1A:
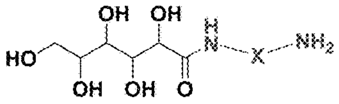

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention. An artisan of ordinary skill in the art need not view, within isolated figure(s), the near infinite number of distinct permutations of features described in the following detailed description to facilitate an understanding of the present invention.

DETAILED DESCRIPTION OF THE INVENTION

In the following detailed description, reference may made to the accompanying drawings, schemes, and structures which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Disclosed herein are methods and compositions for resolving a reverse emulsion in a produced fluid from oil and gas operations. More particularly, one or more polyhydroxy multi-ionic compounds are used in the reverse emulsion breaker compositions for resolving reverse emulsions or complex emulsions in produced fluids in oil and gas operations. These polyhydroxy multi-ionic compounds are derived from polyamines through an aza-Michael Addition reaction between a polyamine and an activated olefin.

Disclosed herein are novel ionic compounds, methods of making the disclosed compounds, and articles, products, or compositions comprising the disclosed compounds. The polyhydroxy multiple charged ionic compounds include multiple positive or negative charges within single molecules that are derived from sugar lactones and water-soluble polyamines to synthesize a gluconoamide intermediate that is then reacted with an ionic monomer through an aza-Michael addition reaction. The compounds have multiple hydroxy groups and multiple ionic groups on the same molecule core providing improved properties of both ionic compounds (e.g., quaternary ammonium compounds) and polyhydroxyl compounds (e.g., polyols) in a single polyhydroxy multi-ionic compound.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

As used herein, the term "and/or", e.g., "X and/or Y" shall be understood to mean either "X and Y" or "X or Y" and shall be taken to provide explicit support for both meanings or for either meaning, e.g. A and/or B includes the options i) A, ii) B or iii) A and B.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Unless defined otherwise, all technical and scientific terms used above have the same meaning as commonly understood by one of ordinary skill in the art to which embodiments of the present invention pertain.

The terms "invention" or "present invention" are not intended to refer to any single embodiment of the particular invention but encompass all possible embodiments as described in the specification and the claims.

The term "about," as used herein, refers to variation in the numerical quantity that can occur, for example, through typical measuring techniques and equipment, with respect to any quantifiable variable, including, but not limited to, mass, volume, time, temperature, pH, and log count of bacteria or viruses. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by $—CH_2CH_2CH_2—$. For alkylene, cycloalkylene, alkynylene, and alkenylene groups, no orientation of the linking group is implied.

The term "alcohol" as used herein refers to —ROH groups. R is absent, a substituted or unsubstituted alkylene, cycloalkylene, alkenylene, alkynylene, arylene, aralkylene, heterocyclylalkylene, or heterocyclylene group as defined herein.

The term "amine" (or "amino") as used herein refers to $—R^1NR^2R^3$ groups. In embodiments, wherein $R^1$, $R^2$, and $R^3$ are independently hydrogen, or a substituted or unsubstituted alkyl, cycloalkyl, alkenyl, alkynyl, aryl, aralkyl, heterocyclylalkyl, or heterocyclyl group as defined herein. In embodiments, $R^1$ is absent, a substituted or unsubstituted alkylene, cycloalkylene, alkenylene, alkynylene, arylene, aralkylene, heterocyclylalkylene, or heterocyclylene group as defined herein. In embodiments, $R^2$ and $R^3$ are independently hydrogen, or a substituted or unsubstituted alkyl, cycloalkyl, alkenyl, alkynyl, aryl, aralkyl, heterocyclylalkyl, or heterocyclyl group as defined herein.

As used herein, the term "antimicrobial" refers to a compound or composition that reduces and/or inactivates a microbial population, including, but not limited to bacteria, viruses, fungi, and algae within about 10 minutes or less, about 8 minutes or less, about 5 minutes or less, about 3 minutes or less, about 2 minutes or less, about 1 minute or less, or about 30 seconds or less. Preferably, the term antimicrobial refers to a composition that provides at least about a 3-log, 3.5 log, 4 log, 4.5 log, or 5 log reduction of a microbial population in about 10 minutes or less, about 8 minutes or less, about 5 minutes or less, about 3 minutes or less, about 2 minutes or less, about 1 minute or less, or about 30 seconds or less.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

The term "carboxylic acid" as used herein refers to —RCOOH groups. R is absent, a substituted or unsubstituted alkylene, cycloalkylene, alkenylene, alkynylene, arylene, aralkylene, heterocyclylalkylene, or heterocyclylene group as defined herein.

The term "ester" as used herein refers to $—RCOOR^1$ group. R is absent, a substituted or unsubstituted alkylene, cycloalkylene, alkenylene, alkynylene, arylene, aralkylene, heterocyclylalkylene, or heterocyclylene group as defined herein. $R^1$ is a substituted or unsubstituted alkyl, cycloalkyl, alkenyl, alkynyl, aryl, aralkyl, heterocyclylalkyl, or heterocyclyl group as defined herein.

The term "ether" as used herein refers to $—ROR^1$ groups. R is absent, a substituted or unsubstituted alkylene, cycloalkylene, alkenylene, alkynylene, arylene, aralkylene, heterocyclylalkylene, or heterocyclylene group as defined herein. $R^1$ is a substituted or unsubstituted alkyl, cycloalkyl, alkenyl, alkynyl, aryl, aralkyl, heterocyclylalkyl, or heterocyclyl group as defined herein.

As used herein, the term "exemplary" refers to an example, an instance, or an illustration, and does not indicate a most preferred embodiment unless otherwise stated.

The term "generally" encompasses both "about" and "substantially."

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

The term "substantially" refers to a great or significant extent. "Substantially" can thus refer to a plurality, majority, and/or a supermajority of said quantifiable variable, given proper context.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents. Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

The term "surfactant" or "surface active agent" refers to an organic chemical that when added to a liquid changes the properties of that liquid at a surface.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Polyhydroxy Multi-Ionic Compounds

The polyhydroxy multi-ionic compounds have the general structure shown in either Formula V or VII:

(V)

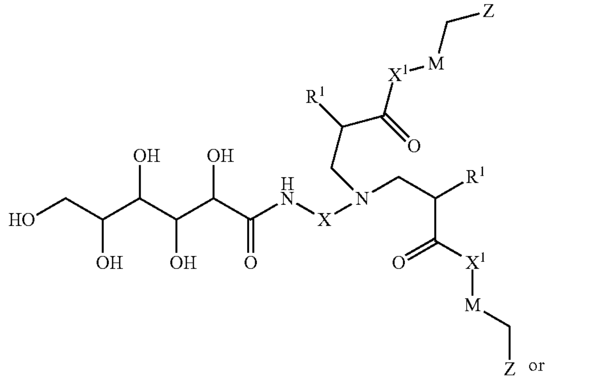

or (VII)

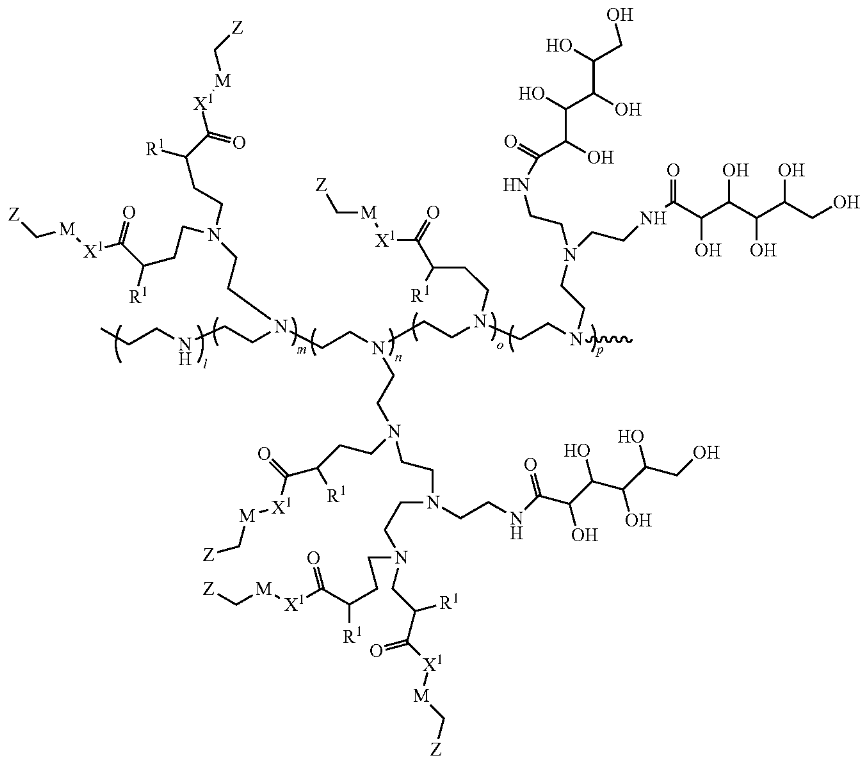

wherein:

l, m, n, o, and p are independently an integer of 0-1000, and wherein at least one of l, m, n, o, and/or p is an integer of 1-1000;

X is $(CH_2)_{m1}$—, —(Ar)—, —$(CH_2Ar)_{m1}$—, —$((CH_2)_{o1}Ar(CH_2)_{o1})_{p1}$—, —$CH_2)_qNH(CH_2)_q)$—, or —$(CH_2NDCH_2)_s$—, wherein D is H,

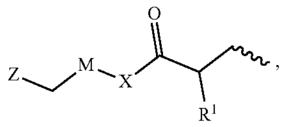

or

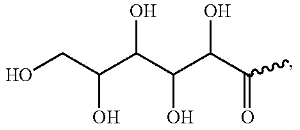

wherein $m_1$, $n_1$, $o_1$, and q are independently an integer from 0 to 10 and $p_1$, r, and s are independently an integer from 1 to 1000;

$X^1$ is NH or O;

$R^1$ is H, $CH_3$, or an unsubstituted, linear or branched C2-C10 alkyl group;

M is absent or an unsubstituted, linear C1-C30 alkylene group;

Z is —$NR^3R^4R^5(+)$ Y(−), —COOH, —$SO_3H$, —$PO_3H$, or a salt thereof; and $R^3$, $R^4$, and $R^5$ are independently C1-C10 alkyl group or benzyl group.

The polyhydroxy multi-ionic compounds have multiple hydroxy groups and multiple ionic groups on the same molecule core.

Methods of Synthesizing Polyhydroxy Multi-Ionic Compounds

The polyhydroxy multi-ionic compounds are made by and are the reaction products of the methods described herein. The synthesis of the polyhydroxy multi-ionic compounds can include first synthesis of a sugar amide (such as gluconoamide) intermediate through amidation followed by an aza-Michael addition reaction between the sugar amide intermediate and cationic/anionic monomers. The sugar amide intermediate is obtained by a process of reacting a sugar lactone with a polyamine. This first amidation step of reacting a sugar lactone with a polyamine is depicted in FIG. 1A, where the sugar lactone (I) is 1,5-D-glucanolactone and the polyamine (II) is Formula $H_2N$—X—$NH_2$, wherein X is —$(CH_2)_{m1}$—, —(Ar)—, —$(CH_2Ar)_{n1}$—, —$((CH_2)_{o1}Ar(CH_2)_{o1})_{p1}$—, —$((CH_2)_qNH(CH_2)_q)_r$—, or —$(CH_2NDCH_2)_s$—, wherein D is H,

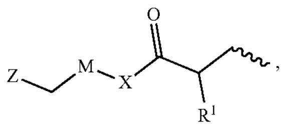

or

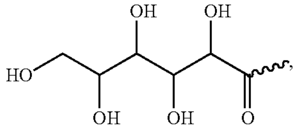

wherein $m_1$, $n_1$, $o_1$, and q are independently an integer from 0 to 10 and $p_1$, r, and s are independently an integer from 1 to 100. The reaction forms the sugar amide intermediates (shown as IIIa or IIIb).

The reaction scheme for this method of preparing the sugar amide can form sugar amide intermediates that are monoamides having the formula (IIIa) or diamides having the formula (IIIb) as shown:

(IIIa)

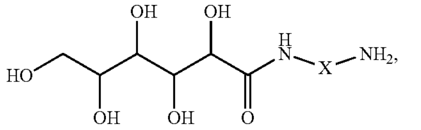

or (IIIb)

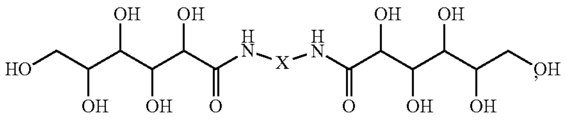

X is —$(CH_2)_{m1}$—, —(Ar)—, —$(CH_2Ar)_{n1}$—, —$((CH_2)_{o1}Ar(CH_2)_{o1})_{p1}$—, or —$((CH_2)_qNH(CH_2)_q)_r$—, —$(CH_2NDCH_2)_s$—, wherein D is H,

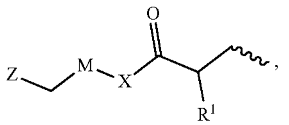

or

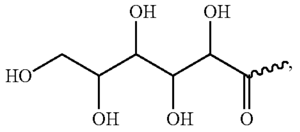

wherein $m_1$, $n_1$, $o_1$, and q are independently an integer from 0 to 10 and $p_1$, r, and s are independently an integer from 1 to 1000.

Figure 1B:
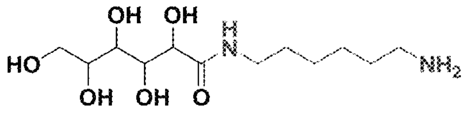
FIG. 1B shows exemplary glucono-monoamides (structures 1-4) and glucono-diamides (structures 5-7).
Figure 1B:
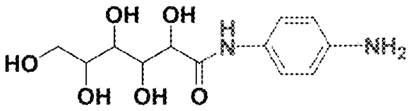
Figure 1B:
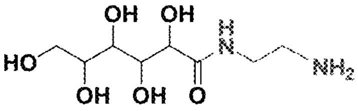
Figure 1B:
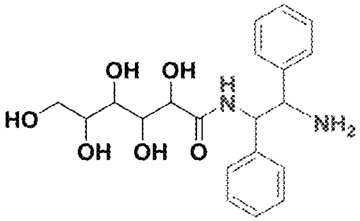
Figure 1B:
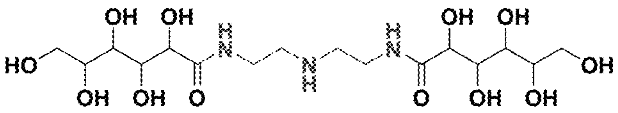
Figure 1B:
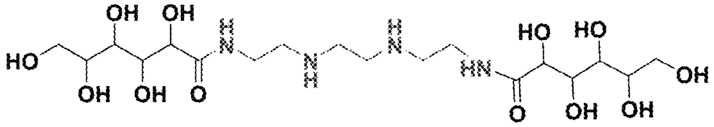
Figure 1B:
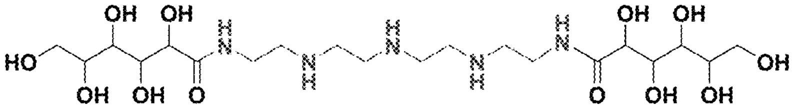

Additional monoamides (IIIa) and diamides (IIIb) are shown in FIG. 1B, where structures 1-4 are monoamides (IIIa) and structures 5-7 are diamides (IIIb). As one skilled in the art will ascertain from the disclosure herein, in additional to monoamides and diamides, depending upon the polyamide (II) used in the reaction, triamides and other polyamide structures can be formed as the intermediates in addition to the structures IIIa and IIb shown. When the sugar amide is formed by the reacting a sugar lactone with a polyamine, the desired molar ratio of sugar lactone to polyamine depends on the number of amine groups in the polyamine and may be about 1:1 or greater per amine group. For example, the molar ratio of sugar lactone to polyamine can be about 2:1 or greater, about 3:1 or greater, about 4:1 or greater per amine group. Preferably, the molar ratio of sugar lactone to polyamine is from about 1:1 to about 4:1, or from about 1:1 to about 2:1, per primary amine group.

Figure 1C:
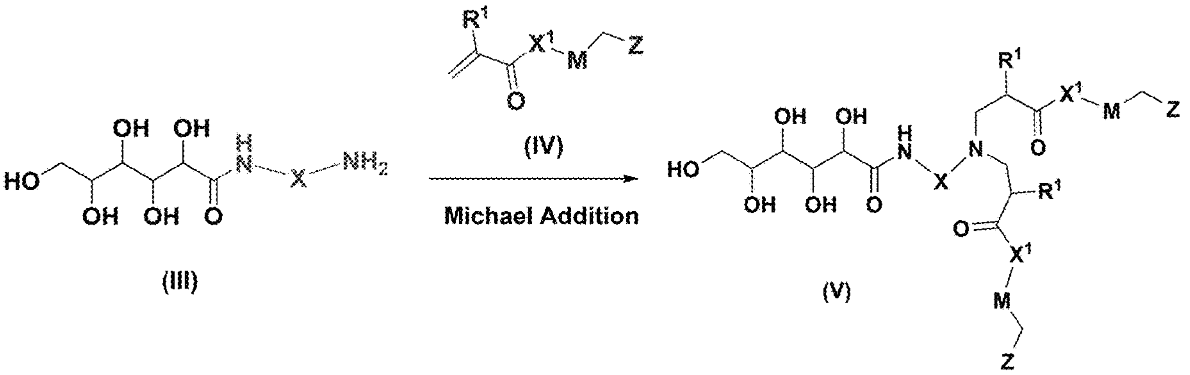
FIG. 1C shows an exemplary aza-Michael addition reaction between a gluconoamide intermediate and a cationic/anionic monomer.

This second step of an aza-Michael addition reaction between the sugar amide intermediate and cationic/anionic monomers is depicted in FIG. 1C, where the sugar amide intermediate is a glucono-monoamide (IIIa), that reacts with a cationic/anionic monomer (IV) to produce a polyhydroxy multi-ionic compound (V). The depicted glucono-monoamide is shown with the general formula IIIa (although diamides, triamides and other polyamide structures can be reacted with the cationic/anionic monomer as depicted in the reaction scheme), wherein X is —$(CH_2)_{m1}$—, —(Ar)—, —$(CH_2Ar)_{n1}$—, —$((CH_2)_{o1}Ar(CH_2)_{o1})_{p1}$—, —$((CH_2)_qNH(CH_2)_q)_r$—, or —$(CH_2NDCH_2)_s$—, wherein D is H,

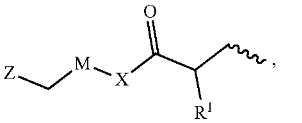

or

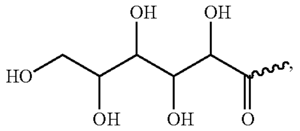

wherein $m_1$, $n_1$, $o_1$, and q are independently an integer from 0 to 10 and $p_1$, r, and s are independently an integer from 1 to 1000, and reacted with the depicted a cationic/anionic monomer (IV), wherein $X^1$ is NH or O, $R^1$ is H, $CH_3$, or an unsubstituted, linear or branched C2-C10 alkyl group, M is absent or an unsubstituted, linear C1-C30 alkylene group, Z is $—NR^3R^4R^5(+)$ Y(−), —COOH, $—SO_3H$, $—PO_3H$, or a salt thereof, and $R^3$, $R^4$, and $R^5$ are independently C1-C10 alkyl group or benzyl group.

The reaction forms the polyhydroxy multi-ionic compound (V), wherein X is $—(CH_2)_{m1}—$, —(Ar)—, $—(CH_2Ar)_{n1}—$, $—((CH_2)_{o1}Ar(CH_2)_{o1})_{p1}—$, $—((CH_2)_qNH(CH_2)_q)_r—$, or $—(CH_2NDCH_2)_s—$, wherein D is H,

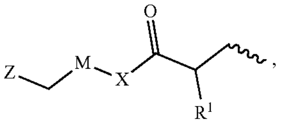

or

-continued

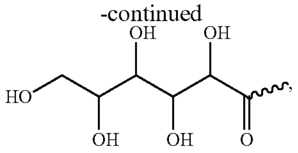

wherein $m_1$, $n_1$, $o_1$, and q are independently an integer from 0 to 10 and $p_1$, r, and s are independently an integer from 1 to 100; $X^1$ is NH or O; $R^1$ is H, $CH_3$, or an unsubstituted, linear or branched C2-C10 alkyl group; M is absent or an unsubstituted, linear C1-C30 alkylene group; Z is $—NR^3R^4R^5(+)$ Y(−), —COOH, $—SO_3H$, $—PO_3H$, or a salt thereof; and $R^3$, $R^4$, and $R^5$ are independently C1-C10 alkyl group or benzyl group.

Figure 2:
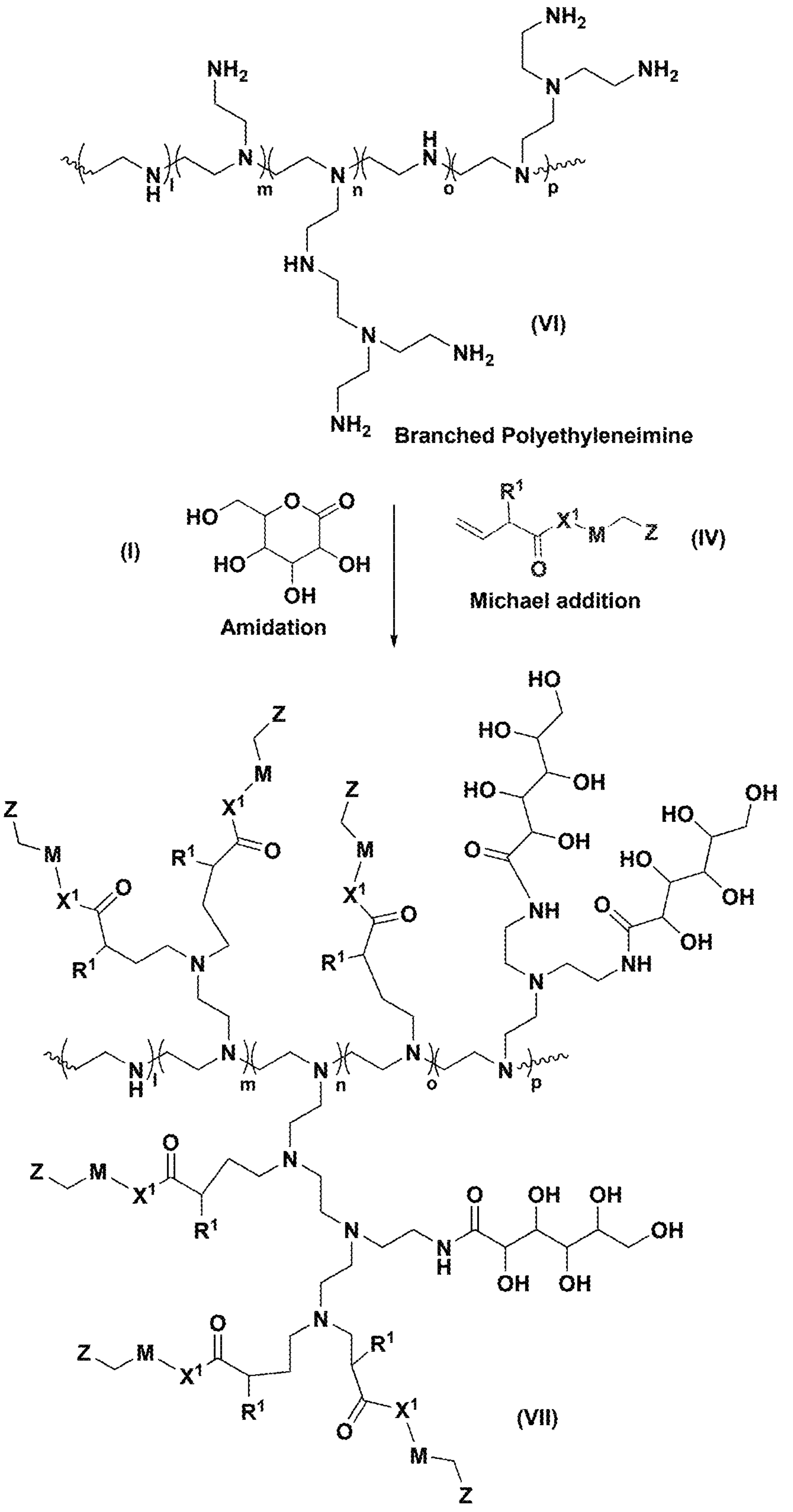
FIG. 2 shows an exemplary synthesis of a polyhydroxy multi-ionic compound using a branched polyethyleneimine.

In additional embodiments, the synthesis of the polyhydroxy multi-ionic compounds disclosed herein can be a single part reaction with simultaneous amidation and aza-Michael addition reactions. The polyhydroxy multi-ionic compounds can be made by and are the reaction products of reacting a polyamine with a sugar lactone and a cationic/anionic monomer. The single step reaction of a polyamine with a sugar lactone and a cationic/anionic monomer is depicted in FIG. 2, where a branched polyamine having the formula generally depicted in VII, wherein l, m, n, o, and p are independently an integer of 0-1000, and wherein at least one of l, m, n, o, and/or p is an integer of 1-100 is reacted with a sugar lactone (I) depicted as 1,5-D-glucanolactone and a cationic/anionic monomer having the formula (IV), wherein $X^1$ is NH or O, $R^1$ is H, $CH_3$, or an unsubstituted, linear or branched C2-C10 alkyl group, M is absent or an unsubstituted, linear C1-C30 alkylene group, Z is $—NR^3R^4R^5(+)$ Y(−), —COOH, $—SO_3H$, $—PO_3H$, or a salt thereof, and $R^3$, $R^4$, and $R^5$ are independently C1-C10 alkyl group or benzyl group, to produce a reaction product having the general structure (VII)

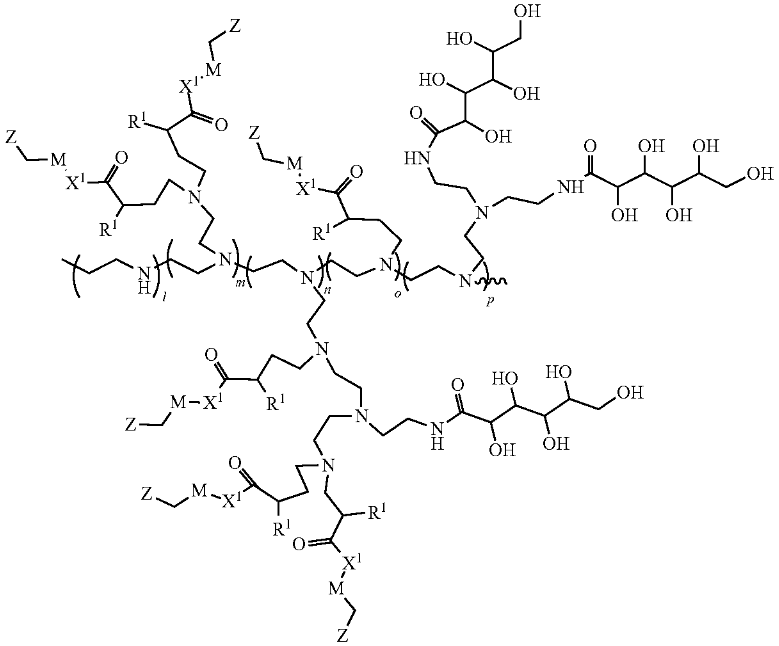

wherein:

l, m, n, o, and p are independently an integer of 0-1000, and wherein at least one of l, m, n, o, and/or p is an integer of 1-1000;

X is $—(CH_2)_{m1}—$, $—(Ar)—$, $—(CH_2Ar)_{n1}—$, $—((CH_2)_{o1}Ar(CH_2)_{o1})_{p1}—$, $—((CH_2)_qNH(CH_2)_q)_r—$, or $—(CH_2NDCH_2)_s—$, wherein D is H,

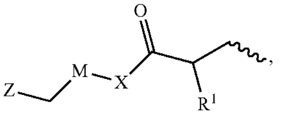

, or

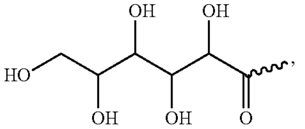

, wherein $m_1$, $n_1$, $o_1$, and q are independently an integer from 0 to 10 and $p_1$, r, and s are independently an integer from 1 to 1000; $X^1$ is NH or O;

$R^1$ is H, $CH_3$, or an unsubstituted, linear or branched C2-C10 alkyl group;

M is absent or an unsubstituted, linear C1-C30 alkylene group;

Z is $—NR^3R^4R^5(+)$ Y(−), —COOH, $—SO_3H$, $—PO_3H$, or a salt thereof; and $R^3$, $R^4$, and $R^5$ are independently C1-C10 alkyl group or benzyl group.

As one skilled in the art will appreciate the reaction of a polethyleneimine, namely branched polethyleneimines as the polyamine, can result in variations of the structure depicted as the polyhydroxy multi-ionic compound having the structure of formula VI, based on the integer values of l, m, n, o, and p which can each independently be an integer of 0-1000, as long as at least one of l, m, n, o, and/or p is an integer of at least 1 such that the produced polyhydroxy multi-ionic compound has at least one opened lactone ring in the structure.

The amine groups undergo an aza-Michael Addition reaction when in contact with an unsaturated hydrocarbon moiety (e.g., carbon-carbon double bond) that is in proximity of an electron withdrawing group such as carbonyl, cyano, or nitro group. Specifically, the aza-Michael addition is a reaction between nucleophiles and cationic or anionic monomers, wherein the nucleophile adds across a carbon-carbon multiple bond that is adjacent to an electron withdrawing and resonance stabilizing activating group, such as a carbonyl group. The aza-Michael addition nucleophile is known as the "Michael donor", the cationic/anionic monomer is the "Michael acceptor", and reaction product is the "Michael adduct."

The reaction can be conducted in the presence of a solvent, and may be conducted at a wide range of temperatures. In embodiments, the reaction can be carried out at a temperature range of about 0° C. to about 200° C., at least about 20° C. to about 150° C., at least about 20° C. to about 120° C., between about 40° C. and about 80° C., or between about 40° C. and about 60° C., or any value there between. The reaction temperature can be about the same from starting of the reaction to end of the reaction or can be changed from one temperature to another while the reaction is going on. The reaction can be conducted at atmospheric pressure.

The reaction time for the synthesis of the compounds disclosed herein can vary widely, depending on such factors as the reaction temperature, presence of a catalyst, the presence or absence of diluent (solvent), and the like. The preferred reaction time can be from about 0.5 hours to about 48 hours, from about 1 hour to about 40 hours, from about 2 hours to about 38 hours, from about 4 hours to about 36 hours, from 6 hours to about 34 hours, from about 8 hours to about 32 hours, from about 10 hours to about 30 hours, from about 12 hours to about 28 hours, from about 14 hours to 26 hours, from about 16 hours to 24 hours, from about 18 hours to 20 hours, from about 1 hour to 8 hours, from 8 hours to 16 hours, from 8 hours to about 24 hours, about 2 hours, about 4 hours, about 6 hours, about 8 hours, about 10 hours, about 14 hours, about 16 hours, about 18 hours, about 24 hours, about 30 hours, about 36 hours, or any values there between.

The reaction for the synthesis of the compounds disclosed herein can go to completion when one mole of the polyamine and at least one mole of the cationic/anionic monomer are mixed together for a sufficient of time at a temperature described above. In embodiments, the synthesis has a high yield of at least about 90%, at least about 910%, at least about 92%, at least about 93%, at least about 94%, at least about 95%, at least about 96%, at least about 97%, at least about 98%, at least about 99%.

The progression of the reaction can be monitored by ESI-MS and/or NMR spectroscopy for consumption of the cationic/anionic monomer. For reactions that proceeded to completion, the formed product can be separated by removal of solvent or by precipitation in a non-polar solvent that was the opposite of the reaction media. For the reactions in water, the formed product is precipitated from the aqueous reaction mixture. Higher pressure can speed-up the reaction.

Sugar Lactones

Sugar lactone used to prepare the sugar amide intermediate may be any suitable sugar lactone. For example, the sugar lactone can be selected from the group consisting of 1,5-D-gluconolactone ($C_6H_{10}O_6$), 1,4-D-galactonolactone, D-mannono-1,4-lactone, ascorbic acid, lactide, d-lactone, d-caprolactone, ε-caprolactone, g-butyrolactone, gulonic acid γ-lactone, b-propiolactone, coumarin, whiskey lactone, and combinations thereof. Preferably, the sugar lactone is 1,5-D-gluconolactone.

Polyamines

The polyamine can have the formula $H_2N—X—NH_2$, wherein X is $—(CH_2)_{m1}—$, $—(Ar)—$, $—(CH_2Ar)_{n1}—$, $—((CH_2)_{o1}Ar(CH_2)_{o1})_{p1}—$, $—((CH_2)_qNH(CH_2)_q)_r—$, or $—(CH_2NDCH_2)_s—$, wherein D is H,

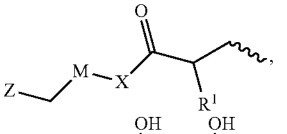

, or

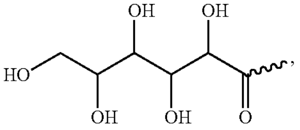

, wherein $m_1$, $n_1$, $o_1$, and q are independently an integer from 0 to 10 and $p_1$, r, and s are independently an integer from 1 to 1000. The polyamine can also have the formula $H_2N—$ X—$NH_2$, wherein X is —$(CH_2)_m$—, wherein m is an integer from 1 to 10, —(Ar)—, —$(CH_2NHCH_2)_n$—, wherein n is an integer from 1 to 100.

A polyamine can have, but is limited to, a generic formula of $NH_2$—$[R^{10'}]_n$—$NH_2$, $(RNH)_n$—$RNH_2$, $H_2N$—$(RNH)_n$—$RNH_2$, or $H_2N$—$(RN(R'))_n$—$RNH_2$, wherein $R^{10'}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNH_2$, $RNHRNH_2$, or $RN(RNH_2)_2$; and n can be from 2 to 1,000,000. The monomer in a polyamine, e.g., the R or R' group, can be the same or different. In this disclosure, a polyamine refers to both small molecule polyamine when n is from 1 to 9 and polymeric polyamine when n is from 10 to 1,000,000. A person skilled in the art appreciates that a diamine is a polyamine having two amino groups.

A polyamine can include polyalkyleneimines, including by not limited to branched, linear, or dendrimer polyethyleneimines. Examples can include diethylenetriamine, triethylenetetraamine, tetraethylenepentamine, pentaethylenehexamine, hexaethyleneheptamine, polyethyleneimines, tris(2-Aminoethyl)amine, ethyleneamine E-100, and mixtures thereof.

In an embodiment the polyamine may be selected from the group consisting of ethylenediamine, 1,6-hexamethylenediamine, diethylenetriamine (DETA), tetraethylenepentamine, 1,3-phenylenediamine, 1,4-phenylenediamine, 1,2-diphenyl-1,2-ethylenediamine, propylenediamine, isopropylenediamine, butylenediamine, piperazine, pentylenediamine piperazine, N,N'-Bis-(2-aminoethyl)piperazine, piperazinoethylethylenediamine, aminoethylpiperazine, triethylenetetramine (TETA), pentaethylenehexamine, hexaethyleneheptamine, tris(2-aminoethyl) amine, dipropylenetriamine, dimethylaminopropylamine, diisopropylenetriamine, dibutylenetriamine, di-sec-butylenetriamine, triethylenetetraamine, tripropylenetetraamine, triisobutylenetetraamine, tetraethylenepentamine, dimethylaminopropylamine polyethylenepolyamine, and combinations thereof.

Other polyamines include diamines and triamines (such as available under the tradename JEFFAMINE® by Huntsman). These highly versatile products contain primary amino groups attached to the end of a polyether backbone normally based on propylene oxide (PO), ethylene oxide (EO), or a mixture of both oxides. JEFFAMINE® amines include a polyetheramine family consisted of monoamines, diamines and triamines based on the core polyether backbone structure. JEFFAMINE® amines also include high-conversion, and polytetramethylene glycol (PTMEG) based polyetheramines. These JEFFAMINE® amines have an average molecular weight (Mw) of from about 130 to about 4,000.

A polyamine can also include a derivative or modified polyamine, in which one or more of the NH protons, but not all, in the polyamine is substituted by an unsubstituted or substituted group. For example, an alkyl polyamine that contains one or more alkyl group connected to the nitrogen atom can be used to produce the polyhydroxy multi-ionic compounds disclosed herein. In these PEI derivatives, only some of primary $NH_2$ or secondary NH protons are replaced by other non-proton groups and the remaining $NH_2$ or NH protons can still react with a Michael acceptor.

One class of the polymeric polyamine includes polyethyleneimine (PEI) and its derivatives. Polyethyleneimine (PEI) or polyaziridine is a polymer with a repeating unit of $CH_2CH_2NH$ and has a general formulation of $NH_2(CH_2CH_2NH)_n$—$CH_2CH_2NH_2$, wherein n can be from 2 to 105. The repeating monomer in PEI has a molecular weight of 43.07 and a nitrogen to carbon ratio of 1:2.

PEIs and their derivatives can linear, branched, or dendric. Linear polyethyleneimines contain all secondary amines, in contrast to branched PEIs which contain primary, secondary and tertiary amino groups. Totally branched, dendrimeric forms also exist and contain primary and tertiary amino groups. Drawings for unmodified linear, branched, and dendrimeric PEI are shown below:

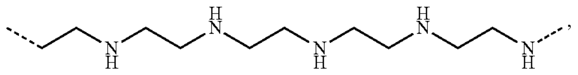

Linear PEI

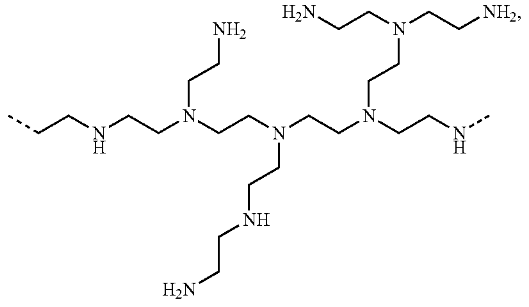

and

Exemplary Branched PEI

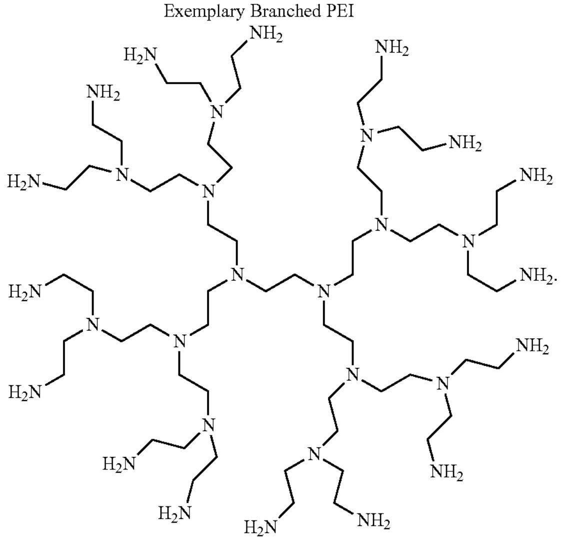

Fully Branched PEI

PEI derivatives are usually obtained by substituting proton(s) on the nitrogen atoms with different group. One such PEI derivative is ethoxylated and propoxylated PEI, wherein the polyethyleneimines are derivatized with ethylene oxide (EO) and/or propylene oxide (PO) side chains. Ethoxylation of PEIs can increase the solubility of PEIs.

PEI is produced on industrial scale. Various commercial polyethyleneimines are available, including for example those sold under the tradename LUPASOL® (BASF), including for example LUPASOL® FG, LUPASOL® G, LUPASOLR PR 8515, LUPASOL® WF, LUPASOL® G 20/35/100, LUPASOL® HF, LUPASOL® P, LUPASOL® PS, LUPASOL® PO 100, LUPASOL® PN 50/60, and LUPASOL® SK. These PEIs have average molecular weights ($M_w$) of about 800, about 1,300, about 2,000, about 5,000, about 25,000, about 1,300/2,000/5,000, about 25,000, about 750,000, about 750,000, about 1,000,000, and about 2,000,000, respectively.

Two commonly used averages for molecular weight of a polymer are number average molecular weight ($M_n$) and weight average molecular weight ($M_w$). The polydispersity index (D) represents the molecular weight distribution of the polymers. $Mn=(\Sigma n_i M_i)/\Sigma n_i$, $M_w=(\Sigma n_i M_i^2)/\Sigma n_i M_i$, and $D=M_w/M_n$, wherein the index number, i, represents the number of different molecular weights present in the sample and $n_i$ is the total number of moles with the molar mass of $M_i$. For a polymer, $M_n$ and $M_w$ are usually different. For example, a PEI compound can have a $M_n$ of about 10,000 by GPC and $M_w$ of about 25,000 by LS.

Light Scattering (LS) can be used to measure Mw of a polymer sample. Another easy way to measure molecular weight of a sample or product is gel permeation chromatography (GPC). GPC is an analytical technique that separates molecules in polymers by size and provides the molecular weight distribution of a material. GPC is also sometimes known as size exclusion chromatography (SEC). This technique is often used for the analysis of polymers for their both Mn and Mw.

These commercially available and exemplary polyethyleneimines are soluble in water and available as anhydrous polyethyleneimines and/or modified polyethyleneimines provided in aqueous solutions or methoxypropanol (as for LUPASOL® PO 100).

Suitable polyethyleneimine useful in the present disclosure may contain a mixture of primary, secondary, and tertiary amine substituents or mixture of different average molecular weights. The mixture of primary, secondary, and tertiary amine substituents may be in any ratio, including for example in the ratio of about 1:1:1 to about 1:2:1 with branching every 3 to 3.5 nitrogen atoms along a chain segment. Alternatively, suitable polyethyleneimine compounds may be primarily one of primary, secondary or tertiary amine substituents.

The polyamine that can be used to make the polyhydroxy multi-ionic compounds disclosed herein can have a wide range of its average molecular weight. Different polyhydroxy multi-ionic compounds with their characteristic average molecular weights can be produced by selecting different starting small molecule polyamines, polymeric PEIs, or mixture thereof. Controlling the size of polyamines or PEI and extent of modification by the activated olefin containing ionic groups, one can produce the polyhydroxy multi-ionic compounds with a similar average molecular weight and multiple cationic charges or multiple anionic charges. Because of this character, one can produce and use different polyhydroxy multi-ionic compounds for a wider range of applications that are using unmodified polyamine or PEIs.

Specifically, the polyamines that can be used to make the polyhydroxy multi-ionic compounds disclosed here have an average molecular weight ($M_w$) of about 60-200, about 100-400, about 100-600, about 600-5,000, about 600-800, about 800-2,000, about 800-5,000, about 100-2,000,000, about 100-25,000, about 600-25,000, about 800-25,000, about 600-750,000, about 800-750,000, about 25,000-750,000, about 750,000-2,000,000, about 100, about 200, about 300, about 400, about 500, about 600, about 700, about 800, about 1,000, about 1,500, about 2,000, about 3,000, about 5,000, about 8,000, about 10,000, about 15,000, about 20,000, about 50,000, about 100,000, about 250,000, about 500,000, about 1,000,000, about 2,000,000, or any value there between.

Cationic/Anionic Monomers

Cationic or anionic monomers can include any α,β-unsaturated carbonyl compounds that have a cationic or anionic group.

The cationic/anionic monomers can have the formula (IV)

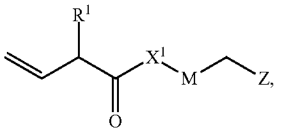

wherein $X^1$ is NH or O; $R^1$ is H, $CH_3$, or an unsubstituted, linear or branched C2-C10 alkyl group; M is absent or an unsubstituted, linear C1-C30 alkylene group; Z is $—NR^3R^4R^5(+)\ Y(-)$, —COOH, $—SO_3H$, $—PO_3H$, or a salt thereof; and $R^3$, $R^4$, and $R^5$ are independently C1-C10 alkyl group or benzyl group.

Examples of cationic monomers include (3-Acrylamidopropyl)trimethylammonium chloride (APTAC), 2-Acrylamido-2-methyl-1-propanesulfonic acid sodium salt (NaAMPS), [3-(Methacryloylamino)propyl]trimethylammonium chloride (MAPTAC), 2-(methacryloyloxy)-N,N,N-trimethylethanaminium chloride (DMAEMA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEMA-MSQ), 2-(acryloyloxy)-N,N,N-trimethylethanaminium chloride (DMAEA-MCQ), and the like.

Examples of anionic monomers include acrylic acid, methacrylic acid, itaconic acid, maleic acid, vinylsulfonic acid, vinylphosphonic acid, 3-(allyloxy)-2-hydroxypropane-1-sulfonate, and the like.

Solvents

The synthesis methods can be conducted in the presence of a solvent and/or diluent. For example, the reaction may comprise a polar solvent. Exemplary solvents for the reaction of a sugar lactone with a polyamine include, for example, water, methanol, ethanol, isopropanol, chloroform, heavy aromatic naphtha, light aromatic naphtha, xylenes, ethylene glycol, methyl carbitol, propylene glycol or a derivative thereof, or polyethylene glycol or a derivative thereof. Preferably, the solvent is methanol or ethylene glycol.

The term "solvent" as used herein refers to any inorganic or organic solvent. Solvents are useful in the disclosed method or composition as reaction solvents or carrier solvents. Solvents include, but are not limited to, oxygenated solvents such as lower alkanols, lower alkyl ethers, glycols, aryl glycol ethers and lower alkyl glycol ethers. Examples of other solvents include, but are not limited to, methanol, ethanol, propanol, isopropanol and butanol, isobutanol, ethylene glycol, diethylene glycol, triethylene glycol, propylene glycol, dipropylene glycol, glycol ethers, mixed ethylene-propylene glycol ethers, ethylene glycol phenyl ether, and propylene glycol phenyl ether. Water is a solvent too. The solvent used herein can be of a single solvent or a mixture of many different solvents. Glycol ethers include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether, and the like, or mixtures thereof.

When a solvent and/or diluent is employed, loading levels can range from as low as about 10 wt-% up to about 80 wt-% and higher. The solvent loading level can be about 0 wt-%, from about 1 wt-% to about 10 wt-%, from about 10 wt-% to about 20 wt-%, from about 20 wt-% to about 30 wt-%, from about 30 wt-% to about 40 wt-%, from about 40 wt-% to about 50 wt-%, from about 50 wt-% to about 60 wt-%, from about 60 wt-% to about 70 wt-%, from about 70 wt-% to about 80 wt-%, from about 1 wt-% to about 20 wt-%, from about 20 wt-% to about 40 wt-%, from about 40 wt-% to about 60 wt-%, from about 60 wt-% to about 80 wt-%, from about 40 wt-% to about 70 wt-%, at least about 5 wt-%, about 15 wt-%, about 25 wt-%, about 35 wt-%, about 45 wt-%, about 55 wt-%, about 65 wt-%, about 75 wt-%, or any value there between of the final reaction mixture.

Catalyst

The synthesis methods can be conducted in the presence of a catalyst. For example, the reaction may comprise a benzyltrimethylammonium hydroxide catalyst. Aza-Michael addition reactions can be catalyzed by a strong acid or base. In some cases, some ionic liquids can function both as reaction media and catalyst. The preferred catalyst for the aza-Michael addition reaction to synthesize the disclosed compounds is a base. Exemplary base catalyst can be hydroxide and amines. Because the reaction to synthesize the disclosed compounds uses a polyamine that usually include a polyamine group, the primary amine group itself can function as a catalyst for the reaction. In such embodiments, no additional catalyst is necessary, or an additional catalyst is optional. Other preferred catalysts include amidine and guanidine bases.

The catalyst loading level can be about 0 wt-%, from about 0.5 wt-% to about 10 wt-%, from about 0.5 wt-% to about 5 wt-%, from about 0.5 wt-% to about 3 wt-%, or any value there between of the final reaction mixture.

Compositions Containing Polyhydroxy Multi-Ionic Compounds and Methods of Use

The polyhydroxy multi-ionic compounds can be provided in a variety of compositions for applications of use, including those described herein. An article, product, or composition can comprise one or more compounds disclosed here or produced by the methods disclosed herein.

Reverse Emulsion Breakers (REB)

In an embodiment, the polyhydroxy multi-ionic compounds can be used as reverse emulsion breakers (REB) or combined with REB compositions including one or more additional reverse emulsion breaker composition agents. The additional reverse emulsion breaker composition agents can include, but are not limited to, an acid, carrier, dispersant, biocide, inorganic salt, organic salt, emulsifier, additional reverse emulsion breaker, corrosion inhibitor, antioxidant, polymer degradation prevention agent, permeability modifier, foaming agent, antifoaming agent, fracturing proppant, glass particulate, sand, fracture proppant/sand control agent, scavenger for $H_2S$, $CO_2$, and/or $O_2$, gelling agent, lubricant, and friction reducing agent, salt, or mixture thereof. Examples of additional components for a REB composition and methods for using a REB are disclosed in U.S. Publication No. 2020/0071265, which is incorporated by reference herein in its entirety.

The additional reverse emulsion breaker composition agent in the disclosed REB compositions can also include, but not be limited to, an organic sulfur compound, de-emulsifier, asphaltene inhibitor, paraffin inhibitor, scale inhibitor, water clarifier, emulsion breaker, reverse emulsion breaker, gas hydrate inhibitor, a pH modifier, a surfactant, or a combination thereof. Furthermore, the additional reverse emulsion breaker composition agent can be a sequestrant, solubilizer, lubricant, buffer, cleaning agent, rinse aid, preservative, binder, thickener or other viscosity modifier, processing aid, carrier, water-conditioning agent, or foam generator, threshold agent or system, aesthetic enhancing agent (e.g., dye, odorant, perfume), or other additive suitable for formulation with a reverse emulsion breaker, or mixtures thereof. The additional reverse emulsion breaker composition agent in a REB composition will vary according to the particular reverse emulsion breaker composition being manufactured and its intend use as one skilled in the art will appreciate. Alternatively, the reverse emulsion breaker composition does not contain or is free of one or more of the additional reverse emulsion breaker composition agents.

When one or more additional reverse emulsion breaker composition agents are used for resolving reverse emulsion or complex emulsion, they can be formulated together with the polyhydroxy multi-ionic compounds derived from the reactions described herein in the same reverse emulsion breaker composition. Alternatively, some or all the additional reverse emulsion breaker composition agents can be formulated into one or more different formulations and be supplied to the produced fluid. In other words, the additional reverse emulsion breaker composition agents can be provided into a produced fluid independently, simultaneously, or sequentially.

Reverse emulsion breaker compositions can be formulated into compositions comprising the following components as shown in Tables 1A-1B. These formulations include the ranges of the components listed and can optionally include additional agents. The values in the Tables below are weight percentages. A skilled artisan will understand the formulations of the Tables below total to 100 wt-%.

TABLE 1A

| Exemplary Reverse Emulsion Breaker Compositions | | | | | | | | | | | | |
|---|---|---|---|---|---|---|---|---|---|---|---|---|
| Component | 1 | 2 | 3 | 4 | 5 | 6 | 7 | 8 | 9 | 10 | 11 | 12 |
| Polyhydroxy Multi-ionic Compound | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Diluent | 5-40 | — | 5-50 | — | 5-50 | 5-50 | 5-40 | — | 5-50 | — | — | 10-20 |
| Corrosion Inhibitor | 0.1-20 | 0.1-20 | — | — | — | — | 0.1-20 | 0.1-20 | — | — | — | 0.1-20 |

TABLE 1A-continued

| Exemplary Reverse Emulsion Breaker Compositions | | | | | | | | | | | | |
|---|---|---|---|---|---|---|---|---|---|---|---|---|
| Component | 1 | 2 | 3 | 4 | 5 | 6 | 7 | 8 | 9 | 10 | 11 | 12 |
| Asphaltene Inhibitor | 0.1-5 | 0.1-5 | 0.1-5 | 0.1-5 | — | — | 0.1-5 | 0.1-5 | 0.1-5 | — | — | 0.1-5 |
| Emulsion Breaker | 1-10 | 1-10 | 1-10 | 1-10 | 1-10 | — | 1-10 | 1-10 | 1-10 | 1-10 | — | 1-10 |
| Gas Hydrate Inhibitor | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | — |
| Water | — | 0-40 | 0-10 | 0-60 | 0-15 | 0-25 | — | 0-40 | 0-10 | 0-65 | 0-75 | — |
| Total | 100 | 100 | 100 | 100 | 100 | 100 | 100 | 100 | 100 | 100 | 100 | 100 |

TABLE 1B

| Exemplary Reverse Emulsion Breaker Compositions | | | | | | | | | | | | |
|---|---|---|---|---|---|---|---|---|---|---|---|---|
| Component | 13 | 14 | 15 | 16 | 17 | 18 | 19 | 20 | 21 | 22 | 23 | 24 |
| Polyhydroxy Multi-ionic Compound | 0.1-20 | 0.1-20 | 0.1-20 | 0.1-20 | 0.1-20 | 0.1-20 | 10-20 | 10-20 | 10-20 | 10-20 | 10-20 | 10-20 |
| Diluent | — | 10-20 | — | 10-35 | 10-35 | — | 10-15 | — | — | 10-35 | 10-35 | — |
| Corrosion Inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene Inhibitor | 0.1-5 | — | — | — | — | — | 0.1-5 | — | — | — | — | — |
| Emulsion Breaker | 1-10 | 1-10 | — | — | 1-10 | — | 1-10 | 1-10 | — | — | — | 1-10 |
| Gas Hydrate Inhibitor | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | — | 0-20 | 0-30 | 0-20 | — | 0-50 |
| Total | 100 | 100 | 100 | 100 | 100 | 100 | 100 | 100 | 100 | 100 | 100 | 100 |

In some embodiments, the reverse emulsion breaker composition or the polyhydroxy multi-ionic compounds disclosed herein may be added to the produced fluid, so the reverse breaker composition in the treated produced fluid is in an amount ranging from about 1 ppm to about 1000 ppm. In other embodiments, the amount of the reverse emulsion breaker composition or the polyhydroxy multi-ionic compounds in the treated produced fluid may range from about 5 ppm to about 200 ppm, from about 10 ppm to about 150 ppm, from about 10 ppm to about 75 ppm, from about 5 ppm to about 50 ppm, from about 5 ppm to about 40 ppm, from about 5 ppm to about 30 ppm, from about 10 ppm to about 60 ppm, from about 10 ppm to about 50 ppm, from about 10 ppm to about 40 ppm, from about 10 ppm to about 75 ppm, from about 20 ppm to about 60 ppm, from about 20 ppm to about 50 ppm, from about 20 ppm to about 40 ppm, or from about 20 ppm to about 30 ppm. In some embodiments, the reverse emulsion breaker composition or the polyhydroxy multi-ionic compounds may be added to the produced fluid, so the reverse emulsion breaker composition or the polyhydroxy multi-ionic compounds have a concentration of from about 10 ppm to about 200 ppm, from about 10 ppm to about 150 ppm, from about 10 ppm to about 100 ppm, or from about 10 ppm to about 75 ppm in the treated produced fluid.

The reverse emulsion breaker composition or the polyhydroxy multi-ionic compounds can be used for breaking reverse emulsion or complex emulsion in a produced fluid in oil and gas applications.

A produced fluid to which the reverse emulsion breaker composition or the polyhydroxy multi-ionic compounds can be introduced into can be an aqueous medium. The aqueous medium can comprise water, gas, oil, and optionally liquid hydrocarbon.

A produced fluid to which the reverse emulsion breaker composition or the polyhydroxy multi-ionic compounds can be introduced can be a liquid comprising hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The produced fluid can be a refined hydrocarbon product.

A produced fluid or gas treated with the reverse emulsion breaker composition or the polyhydroxy multi-ionic compounds can be at any selected temperature, such as ambient temperature or an elevated temperature. The fluid (e.g., liquid hydrocarbon) or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The reverse emulsion breaker composition or the polyhydroxy multi-ionic compounds can be added to a produced fluid at various levels of water cut. For example, the water cut can be from 0% to 100% volume/volume (v/v), from 1% to 80% v/v, or from 1% to 60% v/v. The produced fluid can be an aqueous medium that contains various levels of salinity. The fluid can have a salinity of 0% to 25%, about 1% to 24%, or about 10% to 25% weight/weight (w/w) total dissolved solids (TDS).

The produced fluid or gas in which the reverse emulsion breaker composition or the polyhydroxy multi-ionic compounds are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be a cargo vessel, a storage vessel, a holding tank, or a pipeline connecting the tanks, vessels, or processing units.

The reverse emulsion breaker composition or the polyhydroxy multi-ionic compounds can be introduced into a produced fluid or gas by any appropriate method for ensuring dispersal through the fluid.

The reverse emulsion breaker composition or the polyhydroxy multi-ionic compounds can be added at a point in a flow line upstream from the point at which the produced fluid is processed. The reverse emulsion breaker composition or the polyhydroxy multi-ionic compounds can be injected using mechanical equipment such as chemical injection pumps, piping tees, injection fittings, atomizers, quills, and the like.

The reverse emulsion breaker composition or the polyhydroxy multi-ionic compounds can be pumped into an oil and/or gas pipeline using an umbilical line. A capillary injection system can be used to deliver the reverse emulsion breaker composition or the polyhydroxy multi-ionic compounds to a selected fluid.

The reverse emulsion breaker composition or the polyhydroxy multi-ionic compounds can be introduced into a liquid and a mixture of several liquids, a liquid and gas, liquid, solid, and gas. The reverse emulsion breaker composition or the polyhydroxy multi-ionic compounds can be injected into a gas stream as an aqueous or non-aqueous solution, mixture, or slurry.

The produced fluid or gas can be passed through an absorption tower comprising the reverse emulsion breaker composition or the polyhydroxy multi-ionic compounds.

The reverse emulsion breaker composition or the polyhydroxy multi-ionic compounds can be applied to a produced fluid or gas to provide any selected concentration. In practice, the reverse emulsion breaker composition or the polyhydroxy multi-ionic compounds are typically added to a flow line to provide an effective treating dose of the reverse emulsion breaker composition or the polyhydroxy multi-ionic compounds from about 0.01 to about 5,000 ppm. The reverse emulsion breaker composition or the polyhydroxy multi-ionic compounds can be applied to a produced fluid or gas to provide an active concentration of from about 1 parts per million (ppm) to about 1,000,000 ppm, from about 1 parts per million (ppm) to about 100,000 ppm, or from about 10 ppm to about 75,000 ppm. The polyhydroxy multi-ionic compounds or their salts/compositions can be applied to a fluid to provide an actives concentration of from about 25 ppm to about 10,000 ppm, from about 25 ppm to about 100 ppm, from about 50 ppm to about 100 ppm, from about 100 ppm to about 10,000 ppm, from about 200 ppm to about 8,000 ppm, or from about 500 ppm to about 6,000 ppm. The actives concentration means the concentration of reverse emulsion breaker composition or the polyhydroxy multi-ionic compounds.

The reverse emulsion breaker composition or the polyhydroxy multi-ionic compounds can be applied to a produce fluid or gas to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm in the treated produced fluid. The reverse emulsion breaker composition or the polyhydroxy multi-ionic compounds can be applied to a produced fluid to provide an actives concentration of about 0.125 ppm, about 0.25 ppm, about 0.625 ppm, about 1 ppm, about 1.25 ppm, about 2.5 ppm, about 5 ppm, about 10 ppm, or about 20 ppm in the treated produced fluid. Each produced fluid can have its own dose level requirements, and the effective dose level of the reverse emulsion breaker composition or the polyhydroxy multi-ionic compounds to sufficiently break reverse emulsion or complex emulsion can vary with the produced fluid in which it is used.

The reverse emulsion breaker composition or the polyhydroxy multi-ionic compounds can be applied continuously, in batch, or a combination thereof. The reverse emulsion breaker composition or the polyhydroxy multi-ionic compounds dosing can be continuous. The reverse emulsion breaker composition or the polyhydroxy multi-ionic compounds dosing can be intermittent (e.g., batch treatment) or can be continuous/maintained and/or intermittent.

Dosage rates for continuous treatments typically range from about 10 to about 500 ppm, or from about 10 ppm to about 200 ppm. Dosage rates for batch treatments typically range from about 10 ppm to about 400,000 ppm, or from about 10 ppm to about 20,000 ppm. The reverse emulsion breaker composition or the polyhydroxy multi-ionic compounds can be applied as a pill to a pipeline, providing a high dose (e.g., 20,000 ppm) of the composition.

The flow rate of a flow line in which the reverse emulsion breaker composition or the polyhydroxy multi-ionic compounds is used can be between 0.1 and 100 feet per second, or between 0.1 and 50 feet per second. The reverse emulsion breaker composition or the polyhydroxy multi-ionic compounds can also be formulated with water to facilitate addition to the flow line.

The reverse emulsion breaker composition or the polyhydroxy multi-ionic compounds can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The reverse emulsion breaker composition or the polyhydroxy multi-ionic compounds can be dispensed by immersing either intermittently or continuously in the water or produced fluid. The reverse emulsion breaker composition or the polyhydroxy multi-ionic compounds can then dissolve, for example, at a controlled or predetermined rate. The rate can be effective to maintain a concentration of the dissolved compounds or compositions that are effective for use according to the methods disclosed herein.

Additionally, when the reverse emulsion breaker is used to break an emulsion for a produced fluid in oil and gas operations, an optional emulsion breaker and the reverse emulsion breaker composition can be added to the produced fluid.

The emulsion breaker can comprise an oxyalkylated phenol-formaldehyde resin, a resin ester, an oxyalkylated polyalkylamine, a polyol, a cross-linked polyol with a di- or multi-functional cross linker, an isocyanate, an acid, or a combination thereof. The reverse emulsion breaker composition can comprise a mixture of the reverse emulsion breaker and one or more emulsion breakers, depending on the properties of the produced fluid. In some instances, the emulsion breaker and the reverse emulsion breaker have a synergistic effect for resolving the water-in-oil-in-water emulsion in the produced fluid of an oil production system. The emulsion breaker can have a concentration of from about 100 ppm to about 400 ppm in the produced fluid.

A diluent can be added to the produced fluid and the diluent can be condensate, naphtha, kerosene, light crude oil, or a combination thereof. In some embodiments, a REB composition disclosed herein further comprises a diluent. In some other embodiments, a REB composition disclosed herein further comprises a diluent and one or more emulsion breakers. Suitable diluents suitable for the REB compositions disclosed herein or suitable to be used together with the REB composition disclosed herein include, but are not limited to, naphtha based diluents and synthetic crude oils (SCO). Naphtha based diluents have typical densities of 650-750 $kg/m^3$ and usually are used for a produced fluid with a high content (for example 70 wt-%) of bitumen. SCOs have typical densities of 650-750 $kg/m^3$ and are used with a produced fluid with a low content (for example 50 wt-%) of bitumen. In some embodiments, the diluents suitable for the REB compositions disclosed herein is a combination of C4-C5 hydrocarbons with some aromatic hydrocarbons. The aromatic hydrocarbons vary with according to cost and nature of the produced fluid to be treated.

The reverse emulsion breaker compositions disclosed herein are preferably added to the inlet emulsion to a water and oil separation system. An emulsion breaker, a reverse emulsion breaker, or a combination thereof can be added at an injection point at the inlet pipeline of the produced fluid, before the produced fluid enters one or more separation vessels. When the reverse emulsion breaker is combined with the optional emulsion breaker, they can be injected independently, simultaneously, or sequentially. Further, a diluent can be injected at a different injection point. The separation vessels can be a free water knock out (FWKO) vessel, a heat treater, or a phase separator.

The efficacy of the reverse emulsion breaker composition depends upon a number of factors such as water drop (WD), water quality, interface quality, oil dryness, and the like.

In one aspect, disclosed herein is a composition for resolving a reverse emulsion in a produced fluid from an oil and gas production system, wherein the reverse emulsion breaker composition comprises one or more compounds or their salts disclosed herein and one or more reverse emulsion breaker composition agents. In some embodiments, the reverse emulsion composition breaks oil-in-water emulsion in the produced fluid.

In another aspect, disclosed herein is a method of resolving a reverse emulsion in a produced fluid from an oil and gas production system, wherein the method comprises contacting a produced fluid of an oil and gas production system with a reverse emulsion breaker (REB) composition to generate a treated produced fluid, wherein the reverse emulsion breaker composition comprises one or more compounds disclosed herein and one or more reverse emulsion breaker composition agents. In some embodiments, the reverse emulsion composition breaks oil-in-water emulsion in the produced fluid.

In some embodiments, the produced fluid comprises oil-in-water emulsion, water-in-oil-in-water emulsion, or both. In some other embodiments, the produced fluid comprises crude oil, refined oil, bitumen, condensate, slop oil, distillates, fuels, or mixtures thereof.

In some embodiments, the produced fluid comprises fresh water, recycled water, salt water, surface water, produced water, or mixture thereof. In some embodiments, the produced fluid is one out of petroleum wells, downhole formations, or geothermal wells.

In some embodiments, the produced fluid is from a steam assisted gravity drainage (SAGD) process, and wherein the produced fluid comprises bitumen and water. In some other embodiments, wherein the produced fluid is a produced water, wherein the produced water is water part of the produced fluid after the oil and soils are removed.

In some embodiments, for the methods disclosed herein, providing a REB composition into a produced fluid means that the REB composition or polyhydroxy multi-ionic compounds, or use solution thereof is added into a produced fluid. In some other embodiments, providing a REB composition into a produced fluid means adding the REB composition or polyhydroxy multi-ionic compounds to a fluid which contacts or makes the produced fluid. The REB composition or polyhydroxy multi-ionic compounds, or use solution thereof may be added continuously, or intermittently when more compounds or compositions may be needed.

A use solution of a REB composition or polyhydroxy multi-ionic compounds as used herein refers to a diluted solution for the composition or compounds by a diluent. A diluent as used herein refers to water, a produced fluid, or one of the carriers or solvents defined herein. The REB composition or the compounds can be diluted by a factor of 0.5, 1, 2, 3, 4, 5, 6, 7, 8, 9, 10, 11-1,000,000, or any value there between to generate a use solution and then provide the use solution to a produced fluid. In this disclosure, when a REB composition or polyhydroxy multi-ionic compounds are applied, either the composition/compounds or use solution thereof is applied.

In some embodiments, the reverse emulsion breaker composition is provided to the water system independently, simultaneously, or sequentially with one or more additional reverse emulsion breaker composition agents in the REB composition.

In some embodiments, the REB composition is diluted with water to create a use solution of the REB composition, the use solution is then provided into the produced fluid. In some other embodiments, the water to dilute the REB composition comprises fresh water, recycled water, salt water, surface water, produced water, or mixture thereof. In some embodiments, the water to dilute the REB composition is the produced fluid. Usually, the REB composition or its use solution is injected into the produced fluid. In this situation, the produced fluid is the use solution of the REB compositions. In some embodiments, the concentration of the REB composition is from about 1 ppm to about 1,000 ppm.

Also disclosed herein are methods of breaking an emulsion of water and oil comprising introducing an effective amount of an emulsion breaker composition into contact with the emulsion to destabilize the emulsion, wherein the emulsion breaker composition comprises a polyhydroxy multi-ionic compound as disclosed herein.

Water Clarification

In an embodiment, the polyhydroxy multi-ionic compounds can be used as a water clarifier or combined with water clarification compositions including one or more additional water clarification composition agents. Examples of additional components and methods for water clarification are disclosed in U.S. Publication No. 2020/0071205, which is incorporated by reference herein in its entirety.

The polyhydroxy multi-ionic compounds can be formulated into compositions comprising the following components as shown in Tables 2A-2B. These formulations include the ranges of the components listed and can optionally include additional agents. The values in the Tables below are weight percentages. A skilled artisan will understand the formulations of the Tables below total to 100 wt-%.

TABLE 2A

| Exemplary Water Clarification Compositions | | | | | | | | | | | | |
|---|---|---|---|---|---|---|---|---|---|---|---|---|
| Component | 1 | 2 | 3 | 4 | 5 | 6 | 7 | 8 | 9 | 10 | 11 | 12 |
| Polyhydroxy Multi-ionic Compound | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Organic Solvent | 5-40 | — | 5-50 | — | 5-50 | 5-50 | 5-40 | — | 5-50 | — | — | 10-20 |
| Corrosion Inhibitor | 0.1-20 | 0.1-20 | — | — | — | — | 0.1-20 | 0.1-20 | — | — | — | 0.1-20 |
| Additional Coagulant/ Flocculant | 0.1-5 | 0.1-5 | 0.1-5 | 0.1-5 | — | — | 0.1-5 | 0.1-5 | 0.1-5 | — | — | 0.1-5 |
| Scale Inhibitor | 1-10 | 1-10 | 1-10 | 1-10 | 1-10 | — | 1-10 | 1-10 | 1-10 | 1-10 | — | 1-10 |
| Dispersant | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | — |
| Water | — | 0-40 | 0-10 | 0-60 | 0-15 | 0-25 | — | 0-40 | 0-10 | 0-65 | 0-75 | — |
| Total | 100 | 100 | 100 | 100 | 100 | 100 | 100 | 100 | 100 | 100 | 100 | 100 |

TABLE 2B

| Exemplary Water Clarification Compositions | | | | | | | | | | | | |
|---|---|---|---|---|---|---|---|---|---|---|---|---|
| Component | 13 | 14 | 15 | 16 | 17 | 18 | 19 | 20 | 21 | 22 | 23 | 24 |
| Polyhydroxy Multi-ionic Compound | 0.1-20 | 0.1-20 | 0.1-20 | 0.1-20 | 0.1-20 | 0.1-20 | 10-20 | 10-20 | 10-20 | 10-20 | 10-20 | 10-20 |
| Organic Solvent | — | 10-20 | — | 10-35 | 10-35 | — | 10-15 | — | — | 10-35 | 10-35 | — |
| Corrosion Inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Additional Coagulant/ Flocculant | 0.1-5 | — | — | — | — | — | 0.1-5 | — | — | — | — | — |
| Scale Inhibitor | 1-10 | 1-10 | — | — | 1-10 | — | 1-10 | 1-10 | — | — | — | 1-10 |
| Dispersant | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | — | 0-20 | 0-30 | 0-20 | — | 0-50 |
| Total | 100 | 100 | 100 | 100 | 100 | 100 | 100 | 100 | 100 | 100 | 100 | 100 |

In some embodiments, the water system in the disclosed methods herein is an industrial water system. In some embodiments, the water system is an industrial waste water source or system. In other embodiments, the water system can be, but is not limited to, a cooling water system, including an open recirculating system, closed and once-through cooling water system, boilers and boiler water system, petroleum well system, downhole formation, geothermal well, and other water system in oil and gas field applications, a mineral washing system, flotation and benefaction system, paper mill digester, washer, bleach plant, stock chest, white water system, paper machine surface, black liquor evaporator in the pulp industry, gas scrubber and air washer, continuous casting processes in the metallurgical industry, air conditioning and refrigeration system, process waters, including industrial and petroleum process water, indirect contact cooling and heating water, water reclamation system, water purification system, membrane filtration water system, food processing stream (meat, vegetable, sugar beets, sugar cane, grain, poultry, fruit and soybean), waste treatment system, clarifier, liquid-solid application, municipal sewage treatment, municipal water system, potable water system, aquifer, water tank, sprinkler system, water system used in oil refinery industry, or water heater.

In some embodiments, the water system is a cooling water system, including open recirculating, closed and once-through cooling water system, paper machine surface, food processing stream, waste treatment system, water system used in oil refinery industry, or potable water system. In some embodiments, the water system is a waste water source from a factory, residential home, industrial processing, or like. In some embodiments, the waste water source comprises oil-in-water emulsion. In some embodiments, the waste water source is a water source comprising solid or liquid particles inside water. In some embodiments, the waste water source is an oily waste water from food and beverage, steel, automotive, transportation, refinery, pharmaceutical, metals, paper and pulp, chemical processing, and hydrocarbon processing industries. In other embodiments, the waste water source is an oily waste water from food and beverage process and water system used in oil refinery industry. In yet some other embodiments, the waste water source is an oily waste water in oil and gas operations.

In some embodiments, for the methods disclosed herein, providing a water clarification composition into a water system means that the water clarification composition, polyhydroxy multi-ionic compounds, or a use solution thereof is added into the water system or a fluid of the water system. In other embodiments, providing a water clarification composition into a water system means adding the water clarification composition, polyhydroxy multi-ionic compounds, or a use solution thereof to the water of the water system. In some other embodiments, providing a water clarification composition into a water system means adding the water clarification composition, polyhydroxy multi-ionic compounds, or a use solution thereof to a fluid which contacts or mixes with the water system. The water clarification composition or polyhydroxy multi-ionic compounds may be added continuously, or intermittently when more compounds or compositions may be needed.

A use solution of a water clarification composition or one or more polyhydroxy multi-ionic compounds as used herein refers to a diluted solution for the composition or compounds by a diluent. A diluent as used herein refers to water, the water of the water system, or one of the carriers or solvents defined herein. The water clarification composition or the compounds can be diluted by a factor of 0.5, 1, 2, 3, 4, 5, 6, 7, 8, 9, 10, 11-1,000,000, or any value there between to generate a use solution and then provide the use solution to a water system. In this disclosure, when a composition or polyhydroxy multi-ionic compounds are applied, either the composition/compounds or use solution thereof is applied.

In some embodiments, the water clarification composition or polyhydroxy multi-ionic compounds may be added to the water of the water system in an amount ranging from about 1 ppm to about 1000 ppm. In other embodiments, the amount of the water clarification composition or polyhydroxy multi-ionic compounds in the water of the water system or in the waste water source may range from about 5 ppm to about 100 ppm, about 5 ppm to about 75 ppm, about 5 ppm to about 50 ppm, about 5 ppm to about 40 ppm, about 5 ppm to about 30 ppm, about 10 ppm to about 60 ppm, about 10 ppm to about 50 ppm, about 10 ppm to about 40 ppm, about 10 ppm to about 30 ppm, about 20 ppm to about 60 ppm, about 20 ppm to about 50 ppm, about 20 ppm to about 40 ppm, or about 20 ppm to about 30 ppm, about 25 ppm to about 75 ppm, or about 25 ppm to about 50 ppm. In some embodiments, the water clarification composition or polyhydroxy multi-ionic compounds may be added to the water to an amount ranging from about 100 ppm to about 1000 ppm, about 125 ppm to about 1000 ppm, about 250 ppm to about 1000 ppm, or about 500 ppm to about 1000 ppm.

The water clarification composition or polyhydroxy multi-ionic compounds can be used for clarifying a water system or a waste water source in oil and gas applications such as by treating the water system or waste water source with an effective amount of the compound or composition as described herein. The compounds and compositions can be used in any industry where it is desirable to clarify a water system or water source.

The water clarification composition or polyhydroxy multi-ionic compounds can be used in a condensate/oil systems/gas system, or any combination thereof. For example, the water clarification composition or polyhydroxy multi-ionic compounds can be used in the water of a heat exchanger. The water clarification composition or polyhydroxy multi-ionic compounds can be applied to a liquid produced, or used in the production, transportation, storage, and/or separation of crude oil or natural gas. The water clarification composition or polyhydroxy multi-ionic compounds can be applied to a gas stream used or produced in a coal-fired process, such as a coal-fired power plant.

The water clarification composition or polyhydroxy multi-ionic compounds can be applied to a liquid or waste water source produced or used in a waste-water process, a farm, a slaughter house, a land-fill, a municipality waste-water plant, a coking coal process, or a biofuel process.

A fluid to which the water clarification composition or polyhydroxy multi-ionic compounds can be introduced can be an aqueous medium. The aqueous medium can comprise water, gas, and optionally liquid hydrocarbon.

A fluid to which the water clarification composition or polyhydroxy multi-ionic compounds can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with the water clarification composition or polyhydroxy multi-ionic compounds can be at any selected temperature, such as ambient temperature or an elevated temperature. The fluid (e.g., liquid hydrocarbon) or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The water clarification composition or polyhydroxy multi-ionic compounds can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the water clarification composition or polyhydroxy multi-ionic compounds are introduced can be contained in and/or exposed to diverse types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The water clarification composition or polyhydroxy multi-ionic compounds can be introduced into a fluid or gas of the water system by any appropriate method for ensuring dispersal through the fluid or gas. For examples, the water clarification composition or polyhydroxy multi-ionic compounds can be added to the hydrocarbon fluid before the hydrocarbon fluid contacts the surface.

The water clarification composition or polyhydroxy multi-ionic compounds can be added at a point in a flow line upstream from the point at which water clarification is desired. The water clarification composition or polyhydroxy multi-ionic compounds can be injected using mechanical equipment such as chemical injection pumps, piping tees, injection fittings, atomizers, quills, and the like.

The water clarification composition or polyhydroxy multi-ionic compounds can be pumped into an oil and/or gas pipeline using an umbilical line. A capillary injection system can be used to deliver the water clarification composition or polyhydroxy multi-ionic compounds to a selected fluid.

A fluid to which the water clarification composition or polyhydroxy multi-ionic compounds can be introduced can be an aqueous medium. The aqueous medium can comprise water, gas, and optionally liquid hydrocarbon. A fluid to the water clarification composition or polyhydroxy multi-ionic compounds can be introduced can be a liquid hydrocarbon.

The water clarification composition or polyhydroxy multi-ionic compounds can be introduced into a liquid and a mixture of several liquids, a liquid and gas, liquid, solid, and gas. The water clarification composition or polyhydroxy multi-ionic compounds can be injected into a gas stream as an aqueous or non-aqueous solution, mixture, or slurry.

The fluid or gas can be passed through an absorption tower comprising the water clarification composition or polyhydroxy multi-ionic compounds.

The water clarification composition or polyhydroxy multi-ionic compounds can be applied to a fluid or gas to provide any selected concentration. In practice, the water clarification composition or polyhydroxy multi-ionic compounds are typically added to a flow line to provide an effective treating dose of the water clarification composition or polyhydroxy multi-ionic compounds from about 0.01 ppm to about 5,000 ppm. The water clarification composition or polyhydroxy multi-ionic compounds can be applied to a fluid or gas to provide an active concentration of about 1 parts per million (ppm) to about 1,000,000 ppm, about 1 parts per million (ppm) to about 100,000 ppm, or about 10 ppm to about 75,000 ppm. The polymer salts/compositions can be applied to a fluid to provide an actives concentration of about 100 ppm to about 10,000 ppm, about 200 ppm to about 8,000 ppm, or about 500 ppm to about 6,000 ppm. The actives concentration means the concentration of water clarification composition or polyhydroxy multi-ionic compounds.

The water clarification composition or polyhydroxy multi-ionic compounds can be applied to a water system or a waste water source to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm. The polymer salts/compositions can be applied to a water system or a waste water source to provide an actives concentration of about 0.125 ppm, about 0.25 ppm, about 0.625 ppm, about 1 ppm, about 1.25 ppm, about 2.5 ppm, about 5 ppm, about 10 ppm, or about 20 ppm. Each water system or waste water source can have its own dose level requirements, and the effective dose level of the water clarification composition or polyhydroxy multi-ionic compounds to sufficiently reduce the turbidity of the water system or waste water source can vary with the water system in which it is used.

The water clarification composition or polyhydroxy multi-ionic compounds can be applied continuously, in batch, or a combination thereof. The water clarification composition or polyhydroxy multi-ionic compounds dosing can be continuous. The water clarification composition or polyhydroxy multi-ionic compounds dosing can be intermittent (e.g., batch treatment) or can be continuous/maintained and/or intermittent.

Dosage rates for continuous treatments typically range from about 10 ppm to about 500 ppm, or about 10 ppm to about 200 ppm. Dosage rates for batch treatments typically range from about 10 ppm to about 400,000 ppm, or about 10 ppm to about 20,000 ppm. The water clarification composition or polyhydroxy multi-ionic compounds can be applied as a pill to a pipeline, providing a high dose (e.g., 20,000 ppm) of the composition.

The flow rate of a flow line in which the water clarification composition or polyhydroxy multi-ionic compounds is used can be between 0.1 and 100 feet per second, or between 0.1 and 50 feet per second. The water clarification composition or polyhydroxy multi-ionic compounds can also be formulated with water in order to facilitate addition to the flow line.

The surface can be a part of a wellbore or equipment used in the production, transportation, storage, and/or separation of a fluid such as crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The equipment can comprise a pipeline, a storage vessel, downhole injection tubing, a flow line, or an injection line.

The water clarification composition or polyhydroxy multi-ionic compounds are useful for process or waste water source in the food service or food processing industries.

The water clarification composition or polyhydroxy multi-ionic compounds can also be used for clarifying a water system or waste water source in other industrial process, such as those from heaters, cooling towers, boilers, retort waters, rinse waters, aseptic packaging wash waters, and the like.

The water clarification composition or polyhydroxy multi-ionic compounds can be used to treat a water or waste water source from janitorial and/or housekeeping applications, food processing, and in laundry applications.

The water clarification composition or polyhydroxy multi-ionic compounds can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The water clarification composition or polyhydroxy multi-ionic compounds can be dispensed by immersing either intermittently or continuously into the water, fluid, or gas of the water system. The water clarification composition or polyhydroxy multi-ionic compounds can then dissolve, for example, at a controlled or predetermined rate. The rate can be effective to maintain a concentration of the dissolved compounds or compositions that are effective for use according to the methods disclosed herein.

Also disclosed herein are methods of clarifying a water source, such as waste water, comprising introducing an effective amount of a waste water clarification composition into contact with the water source, wherein the waste water clarification composition comprises a polyhydroxy multi-ionic compound as disclosed herein.

Clay Stabilization

In an embodiment, the polyhydroxy multi-ionic compounds can be used as a clay stabilizers or combined with clay stabilization compositions including one or more additional clay stabilization composition agents. Examples of additional components and methods for clay stabilization are disclosed in U.S. Publication No. 2020/0071602, which is incorporated by reference herein in its entirety.

The polyhydroxy multi-ionic compounds can be formulated into compositions comprising the following components as shown in Tables 3A-3E. These formulations include the ranges of the components listed and can optionally include additional agents. The values in the Tables below are weight percentages. A skilled artisan will understand the formulations of the Tables below total to 100 wt-%.

TABLE 3A

Exemplary Clay Treatment Compositions

| Component | 1 | 2 | 3 | 4 | 5 | 6 | 7 | 8 |
|---|---|---|---|---|---|---|---|---|
| Polyhydroxy Multi-ionic Compound | 0.025-0.2 | 0.025-0.2 | 0.025-0.2 | 0.025-0.2 | 0.025-0.2 | 0.025-0.2 | 0.025-0.2 | 0.025-0.2 |
| Friction Reducer | 0.025-0.4 | — | 0.025-0.4 | 0.025-0.4 | 0.025-0.4 | 0.025-0.4 | — | — |
| Flowback Aid | 0.025-0.2 | 0.025-0.2 | — | 0.025-0.2 | 0.025-0.2 | 0.025-0.2 | — | 0.025-0.2 |
| Viscosifier | 0.025-1 | 0.025-1 | 0.025-1 | 0.025-1 | 0.025-1 | 0.025-1 | 0.025-1 | 0.025-1 |
| Crosslinker | 0.010-0.3 | 0.010-0.3 | 0.010-0.3 | — | 0.010-0.3 | 0.010-0.3 | 0.010-0.3 | — |
| Scale Inhibitor | 0.025-0.2 | 0.025-0.2 | 0.025-0.2 | 0.025-0.2 | — | 0.025-0.2 | 0.025-0.2 | 0.025-0.2 |
| Biocide | 0.025-0.2 | 0.025-0.2 | 0.025-0.2 | 0.025-0.2 | 0.025-0.2 | — | 0.025-0.2 | 0.025-0.2 |
| Water | 97.5-99.84 | 97.9-99.865 | 97.7-99.865 | 97.8-99.85 | 97.7-99.865 | 97.7-99.865 | 98.1-99.89 | 98.2-99.875 |
| Total | 100 | 100 | 100 | 100 | 100 | 100 | 100 | 100 |

TABLE 3B

Exemplary Clay Treatment Compositions

| Component | 9 | 10 | 11 | 12 | 13 |
|---|---|---|---|---|---|
| Polyhydroxy Multi-ionic Compound | 0.025-0.2 | 0.025-0.2 | 0.025-0.2 | 0.025-0.2 | 0.025-0.2 |
| Friction Reducer | — | — | 0.025-0.4 | 0.025-0.4 | 0.025-0.4 |
| Flowback Aid | 0.025-0.2 | 0.025-0.2 | — | — | — |

TABLE 3B-continued

| Exemplary Clay Treatment Compositions | | | | | |
|---|---|---|---|---|---|
| Viscosifier | 0.025-1 | 0.025-1 | 0.025-1 | 0.025-1 | 0.025-1 |
| Crosslinker | 0.010-0.3 | 0.010-0.3 | — | 0.010-0.3 | 0.010-0.3 |
| Scale Inhibitor | — | 0.025-0.2 | 0.025-0.2 | — | 0.025-0.2 |
| Biocide | 0.025-0.2 | — | 0.025-0.2 | 0.025-0.2 | — |
| Water | 98.1-99.89 | 98.1-99.89 | 98-99.875 | 97.9-99.89 | 97.7-99.89 |
| Total | 100 | 100 | 100 | 100 | 100 |

| Component | 14 | 15 | 16 | 17 |
|---|---|---|---|---|
| Polyhydroxy Multi-ionic Compound | 0.025-0.2 | 0.025-0.2 | 0.025-0.2 | 0.025-0.2 |
| Friction Reducer | 0.025-0.4 | 0.025-0.4 | 0.025-0.4 | 0.025-0.4 |
| Flowback Aid | 0.025-0.2 | 0.025-0.2 | 0.025-0.2 | 0.025-0.2 |
| Viscosifier | — | 0.025-1 | 0.025-1 | 0.025-1 |
| Crosslinker | — | — | — | 0.010-0.3 |
| Scale Inhibitor | 0.025-0.2 | — | 0.025-0.2 | — |
| Biocide | 0.025-0.2 | 0.025-0.2 | — | — |
| Water | 98.8-99.875 | 98-99.875 | 98-99.865 | 97.9-99.89 |
| Total | 100 | 100 | 100 | 100 |

TABLE 3C

| Exemplary Clay Treatment Compositions | | | | | | | | |
|---|---|---|---|---|---|---|---|---|
| Component | 18 | 19 | 20 | 21 | 22 | 23 | 24 | 25 |
| Polyhydroxy Multi-ionic Compound | 0.025-0.2 | 0.025-0.2 | 0.025-0.2 | 0.025-0.2 | 0.025-0.2 | 0.025-0.2 | 0.025-0.2 | 0.025-0.2 |
| Friction Reducer | — | — | — | 0.025-0.4 | 0.025-0.4 | 0.025-0.4 | 0.025-0.4 | 0.025-0.4 |
| Flowback Aid | — | — | — | — | — | — | — | 0.025-0.2 |
| Viscosifier | 0.025-1 | 0.025-1 | 0.025-1 | — | 0.025-1 | 0.025-1 | 0.025-1 | — |
| Crosslinker | — | 0.010-0.3 | 0.010-0.3 | — | — | — | 0.010-0.3 | — |
| Scale Inhibitor | 0.025-0.2 | — | 0.025-0.2 | 0.025-0.2 | — | 0.025-0.2 | — | — |
| Biocide | 0.025-0.2 | 0.025-0.2 | — | 0.025-0.2 | 0.025-0.2 | — | — | 0.025-0.2 |
| Water | 98.4-99.9 | 98.3-99.915 | 98.3-99.915 | 99-99.9 | 98.2-99.9 | 98.2-99.9 | 98.1-99.915 | 99-99.9 |
| Total | 100 | 100 | 100 | 100 | 100 | 100 | 100 | 100 |

TABLE 3D

| Exemplary Clay Treatment Compositions | | | | | | | | |
|---|---|---|---|---|---|---|---|---|
| Component | 26 | 27 | 28 | 29 | 30 | 31 | 32 | 33 |
| Polyhydroxy Multi-ionic Compound | 0.025-0.2 | 0.025-0.2 | 0.025-0.2 | 0.025-0.2 | 0.025-0.2 | 0.025-0.2 | 0.025-0.2 | 0.025-0.2 |
| Friction Reducer | 0.025-0.4 | 0.025-0.4 | — | — | — | 0.025-0.4 | 0.025-0.4 | 0.025-0.4 |
| Flowback Aid | 0.025-0.2 | 0.025-0.2 | — | — | — | — | — | — |

TABLE 3D-continued

| Exemplary Clay Treatment Compositions | | | | | | | | |
|---|---|---|---|---|---|---|---|---|
| Component | 26 | 27 | 28 | 29 | 30 | 31 | 32 | 33 |
| Viscosifier | — | 0.025-1 | 0.025-1 | 0.025-1 | 0.025-1 | — | — | 0.025-1 |
| Crosslinker | — | — | — | — | 0.010-0.3 | — | — | — |
| Scale Inhibitor | 0.0250.2- | — | — | | — | — | 0.025-0.2 | — |
| Biocide | — | — | 0.025-0.2 | — | — | 0.025-0.2 | — | — |
| Water | 99-99.9 | 98.2-99.9 | 98.6-99.925 | 98.6-99.925 | 98.5-99.94 | 99.2-99.925 | 99.2-99.925 | 98.4-99.925 |
| Total | 100 | 100 | 100 | 100 | 100 | 100 | 100 | 100 |

TABLE 3E

| Exemplary Clay Treatment Compositions | | | |
|---|---|---|---|
| Component | 34 | 35 | 36 |
| Polyhydroxy Multi-ionic Compound | 0.025-0.2 | 0.025-0.2 | 0.025-0.2 |
| Friction Reducer | 0.025-0.4 | 0.025-0.4 | — |
| Flowback Aid | 0.025-0.2 | — | — |
| Viscosifier | — | — | 0.025-1 |
| Crosslinker | — | — | — |
| Scale Inhibitor | — | — | — |
| Biocide | — | — | — |
| Water | 99.2-99.925 | 99.4-99.95 | 98.8-99.95 |
| Total | 100 | 100 | 100 |

In some embodiments, the clay treatment composition or the polyhydroxy multi-ionic compounds may be added to a fluid or stimulation fluid for oil and gas operations, so the concentration of the composition or the compound in the fluid or stimulation fluid is from about 1 ppm to about 2,000 ppm or from about 400 ppm to about 7,000 ppm. In other embodiments, the amount of the clay treatment composition or the polyhydroxy multi-ionic compounds in the fluid may range from about 5 ppm to about 2,000 ppm, from about 50 ppm to about 2,000 ppm, from about 100 ppm to about 2,000 ppm, from about 200 ppm to about 2,000 ppm, from about 250 ppm to about 2,000 ppm, from about 300 ppm to about 2,000 ppm, from about 400 ppm to about 2,000 ppm, from about 100 ppm to about 1,000 ppm, from about 200 ppm to about 800 ppm, from about 300 ppm to about 700 ppm, from about 400 ppm to about 600 ppm, or from about 100 ppm to about 500 ppm. In some embodiments, the clay treatment composition or the polyhydroxy multi-ionic compounds may be added to the water of the subterranean formation to an amount ranging from about 50 ppm to about 2,000 ppm, from about 100 ppm to about 500 ppm, from about 250 ppm to about 2,000 ppm, or from about 200 ppm to about 800 ppm.

The clay treatment composition or the polyhydroxy multi-ionic compounds can be applied to any fluid or stimulation fluid used in crude oil or natural gas productions. A fluid to which the clay treatment composition or the polyhydroxy multi-ionic compounds can be introduced can be an aqueous medium. The aqueous medium can comprise water, oil, and optionally liquid hydrocarbon.

A fluid or gas treated with the clay treatment composition or the polyhydroxy multi-ionic compounds can be at any selected temperature, such as ambient temperature or an elevated temperature. The fluid (e.g., liquid hydrocarbon) or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The clay treatment composition or the polyhydroxy multi-ionic compounds can be added to a fluid or stimulation fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The clay treatment composition or the polyhydroxy multi-ionic compounds can be introduced into a fluid, stimulation fluid, or gas by any appropriate method for ensuring dispersal through the fluid or gas. For examples, the clay treatment composition or the polyhydroxy multi-ionic compounds can be added to a drilling fluid or stimulation fluid before the drilling or stimulation fluid contacts the subterranean formation.

The clay treatment composition or the polyhydroxy multi-ionic compounds can be added at a point in a flow line upstream from the point at which the fluid is used for oil and gas productions. The clay treatment composition or the polyhydroxy multi-ionic compounds can be injected using mechanical equipment such as chemical injection pumps, piping tees, injection fittings, atomizers, quills, and the like. The clay treatment composition or the polyhydroxy multi-ionic compounds can be pumped into an oil and/or gas pipeline using an umbilical line. A capillary injection system can be used to deliver the clay treatment composition or the polyhydroxy multi-ionic compounds to a selected fluid.

A fluid to which the clay treatment composition or the polyhydroxy multi-ionic compounds can be introduced can be an aqueous medium. The aqueous medium can comprise water, oil, and optionally liquid hydrocarbon. A fluid to the clay treatment composition or the polyhydroxy multi-ionic compounds can be introduced can be fracturing fluid, acidizing fluid, drilling fluid, drill-in fluid, stimulation fluid, gravel pack fluid, completion fluid, cementing fluid, other oil gas operation fluid, any other fluid for oil and gas production, or mixture thereof.

The clay treatment composition or the polyhydroxy multi-ionic compounds can be introduced into a liquid and a mixture of several liquids, a liquid and gas, liquid, solid, and gas. The clay treatment composition or the polyhydroxy multi-ionic compounds can be injected into a gas stream as an aqueous or non-aqueous solution, mixture, or slurry.

The fluid or gas can be passed through an absorption tower comprising the clay treatment composition or the polyhydroxy multi-ionic compounds.

The clay treatment composition or the polyhydroxy multi-ionic compounds can be applied to a fluid or gas to provide any selected concentration. In practice, the clay treatment composition or the polyhydroxy multi-ionic compounds are typically added to a flow line to provide an effective treating dose of the clay treatment composition or the polyhydroxy multi-ionic compounds from about 0.01 ppm to about 5,000 ppm. The clay treatment composition or the polyhydroxy multi-ionic compounds can be applied to a fluid or gas to provide an active concentration of about 1 parts per million (ppm) to about 1,000,000 ppm, from about 1 parts per million (ppm) to about 100,000 ppm, or from about 10 ppm to about 75,000 ppm. The polymer salts/compositions can be applied to a fluid to provide an actives concentration of from about 100 ppm to about 10,000 ppm, from about 200 ppm to about 8,000 ppm, or from about 500 ppm to about 6,000 ppm. The actives concentration means the concentration of clay treatment composition or the polyhydroxy multi-ionic compounds.

The clay treatment composition or the polyhydroxy multi-ionic compounds can be applied to a fluid or gas to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm. The polyhydroxy multi-ionic compounds, their salt or clay treatment composition can be applied to a fluid or gas to provide an actives concentration of about 0.125 ppm, about 0.25 ppm, about 0.625 ppm, about 1 ppm, about 1.25 ppm, about 2.5 ppm, about 5 ppm, about 10 ppm, about 20 ppm, about 40 ppm, about 60 ppm, about 100 ppm, about 200 ppm, about 400 ppm, about 600 ppm, about 800 ppm, about 1,000 ppm in the fluid or gas. Each fluid can have its own dose level requirements, and the effective dose level of the clay treatment composition or the polyhydroxy multi-ionic compounds to sufficiently prevent clay swell, clay migration, or sludge formation can vary with the subterranean system in which it is used.

The clay treatment composition or the polyhydroxy multi-ionic compounds can be applied continuously, in batch, or a combination thereof. The clay treatment composition or the polyhydroxy multi-ionic compounds dosing can be continuous. The clay treatment composition or the polyhydroxy multi-ionic compounds dosing can be intermittent (e.g., batch treatment) or can be continuous/maintained and/or intermittent.

Dosage rates for continuous treatments typically range from about 10 ppm to about 500 ppm, or from about 10 ppm to about 200 ppm. Dosage rates for batch treatments typically range from about 10 ppm to about 400,000 ppm, or from about 10 to about 20,000 ppm. The clay treatment composition or the polyhydroxy multi-ionic compounds can be applied as a pill to a pipeline, providing a high dose (e.g., 20,000 ppm) of the composition.

The flow rate of a flow line in which the clay treatment composition or the polyhydroxy multi-ionic compounds is used can be between about 0.1 feet per second and about 100 feet per second, or between about 0.1 feet per second and about 50 feet per second. The clay treatment composition or the polyhydroxy multi-ionic compounds can also be formulated with water to facilitate addition to the flow line.

The clay treatment composition or the polyhydroxy multi-ionic compounds can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The clay treatment composition or the polyhydroxy multi-ionic compounds can be dispensed by immersing either intermittently or continuously in a fluid used in oil and gas productions. The clay treatment composition or the polyhydroxy multi-ionic compounds can then dissolve, for example, at a controlled or predetermined rate. The rate can be effective to maintain a concentration of the dissolved compounds or compositions that are effective for use according to the methods disclosed herein.

The clay treatment composition disclosed herein can comprise from about 10 wt-% to about 90 wt-% of the additional clay treatment composition agent(s) and from about 10 wt-% to about 90 wt-% of one or more polyhydroxy multi-ionic compounds. The clay treatment composition disclosed herein can comprise from about 20 wt-% to about 80 wt-% of the carrier, biocide, corrosion inhibitor, additional clay treatment composition agent, a combination thereof, from about 20 wt-% to about 80 wt-% of one or more polyhydroxy multi-ionic compounds, from about 30 wt-% to about 70 wt-% of the carrier, biocide, corrosion inhibitor, additional clay treatment composition agent, a combination thereof and from about 30 wt-% to about 70 wt-% of one or more polyhydroxy multi-ionic compounds, from about 40 wt-% to about 60 wt-% of the carrier, biocide, corrosion inhibitor, additional clay treatment composition agent, a combination thereof and from about 40 wt-% to about 60 wt. % water; or from about 40 wt-% to about 60 wt-% of one or more polyhydroxy multi-ionic compounds, from about 10 wt-% to about 20 wt-% of the biocide, corrosion inhibitor, additional clay treatment composition agent, a combination thereof and from about 20 wt-% to about 60 wt. % water. The clay treatment composition can comprise one or more additional clay stabilizers depending on the properties of the subterranean formation.

In some instances, the multiple charged cationic compound and the additional clay treatment composition agent have a synergistic effect for preventing clay swell, clay migration, and sludge formation in a specific subterranean formation.

Also disclosed herein are methods of clay treatment (i.e. stabilizing swellable clays and/or reducing formation of sludge in a subterranean formation) comprising introducing an effective amount of a clay treatment composition into a subterranean formation with the fluid, wherein the clay treatment composition comprises a polyhydroxy multi-ionic compound as disclosed herein, and stabilizes swellable clays and reduces formation of sludge, or both.

Biofilm Inhibitors

In an embodiment, the polyhydroxy multi-ionic compounds can be used for microbial fouling or biofilm control in a water system composition including one or more additional fouling control composition agents. Examples of additional components and methods for microbial fouling or biofilm control in a water system are disclosed in U.S. Pat. No. 11,155,481, which is incorporated by reference herein in its entirety.

The polyhydroxy multi-ionic compounds can be formulated into compositions comprising the following components as shown in Tables 4A-4B. These formulations include the ranges of the components listed and can optionally include additional agents. The values in the Tables below are weight percentages. A skilled artisan will understand the formulations of the Tables below total to 100 wt-%.

TABLE 4A

| Exemplary Fouling Control Compositions | | | | | | | | | | | | |
|---|---|---|---|---|---|---|---|---|---|---|---|---|
| Component | 1 | 2 | 3 | 4 | 5 | 6 | 7 | 8 | 9 | 10 | 11 | 12 |
| Polyhydroxy Multi-ionic Compound | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Surfactant | 5-40 | — | 5-50 | — | 5-50 | 5-50 | 5-40 | — | 5-50 | — | — | 10-20 |
| Corrosion Inhibitor | 0.1-20 | 0.1-20 | — | — | — | — | 0.1-20 | 0.1-20 | — | — | — | 0.1-20 |
| Preservative | 0.1-5 | 0.1-5 | 0.1-5 | 0.1-5 | — | — | 0.1-5 | 0.1-5 | 0.1-5 | — | — | 0.1-5 |
| Scale Inhibitor | 1-10 | 1-10 | 1-10 | 1-10 | 1-10 | — | 1-10 | 1-10 | 1-10 | 1-10 | — | 1-10 |
| Water Clarifier | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | — |
| Water | — | 0-40 | 0-10 | 0-60 | 0-15 | 0-25 | — | 0-40 | 0-10 | 0-65 | 0-75 | — |
| Total | 100 | 100 | 100 | 100 | 100 | 100 | 100 | 100 | 100 | 100 | 100 | 100 |

TABLE 4B

| Exemplary Fouling Control Compositions | | | | | | | | | | | | |
|---|---|---|---|---|---|---|---|---|---|---|---|---|
| Component | 13 | 14 | 15 | 16 | 17 | 18 | 19 | 20 | 21 | 22 | 23 | 24 |
| Polyhydroxy Multi-ionic Compound | 0.1-20 | 0.1-20 | 0.1-20 | 0.1-20 | 0.1-20 | 0.1-20 | 10-20 | 10-20 | 10-20 | 10-20 | 10-20 | 10-20 |
| Surfactant | — | 10-20 | — | 10-35 | 10-35 | — | 10-15 | — | — | 10-35 | 10-35 | — |
| Corrosion Inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Preservative | 0.1-5 | — | — | — | — | — | 0.1-5 | — | — | — | — | — |
| Scale Inhibitor | 1-10 | 1-10 | — | — | 1-10 | — | 1-10 | 1-10 | — | — | — | 1-10 |
| Water Clarifier | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | — | 0-20 | 0-30 | 0-20 | — | 0-50 |
| Total | 100 | 100 | 100 | 100 | 100 | 100 | 100 | 100 | 100 | 100 | 100 | 100 |

In an embodiment, the polyhydroxy multi-ionic compounds can be used as biofilm inhibitors or combined with biofilm inhibiting compositions including one or more additional biofilm inhibiting composition agents. Also disclosed herein are methods of reducing fouling and biofilm inhibition (or treatment) comprising introducing an effective amount of a bio-film inhibitor, wherein the bio-film inhibitor comprises a polyhydroxy multi-ionic compound as disclosed herein.

In some embodiments, the water system in the disclosed methods herein is an industrial water system. In other embodiments, the water system can be, but is not limited to, a cooling water system, including an open recirculating system, closed and once-through cooling water system, boilers and boiler water system, petroleum well system, downhole formation, geothermal well, and other water system in oil and gas field applications, a mineral washing system, flotation and benefaction system, paper mill digester, washer, bleach plant, stock chest, white water system, paper machine surface, black liquor evaporator in the pulp industry, gas scrubber and air washer, continuous casting processes in the metallurgical industry, air conditioning and refrigeration system, industrial and petroleum process water, indirect contact cooling and heating water, water reclamation system, water purification system, membrane filtration water system, food processing stream (meat, vegetable, sugar beets, sugar cane, grain, poultry, fruit and soybean), waste treatment system, clarifier, liquid-solid application, municipal sewage treatment, municipal water system, potable water system, aquifer, water tank, sprinkler system, or water heater.

In some embodiments, the water system is a cooling water system, including open recirculating, closed and once-through cooling water system, paper machine surface, food processing stream, waste treatment system, or potable water system. In some embodiments, the water system is any system including a wetable surface. Examples of such water systems include, but are not limited to, walls and floors of bathrooms, surfaces of foods and vegetables, and processing fluid for food. Such surfaces are typically in constant contact with water or water moisture and subjected to biofilm growth.

In some embodiments, for the methods disclosed herein, providing a fouling control composition into a water system means that the fouling control composition or polyhydroxy multi-ionic compounds are added into a fluid comprising water or surfaces of a water system. In other embodiments, providing a fouling control composition into a water system means adding the fouling control composition or polyhydroxy multi-ionic compounds to the surface or water of the water system. In some other embodiments, providing a fouling control composition into a water system means adding the fouling control composition or polyhydroxy multi-ionic compounds to a fluid or gas which contacts the surfaces of the water system. The fouling control composition or polyhydroxy multi-ionic compounds may be added continuously, or intermittently when more compounds or compositions may be needed.

In some embodiments, the fouling control composition or polyhydroxy multi-ionic compounds may be added to the water of the water system in an amount ranging from about 1 ppm to about 1000 ppm. In other embodiments, the amount of the fouling control composition or polyhydroxy multi-ionic compounds in the water of the water system may range from about 5 ppm to about 100 ppm, from about 5 ppm to about 50 ppm, from about 5 ppm to about 40 ppm, from about 5 ppm to about 30 ppm, from about 10 ppm to about 60 ppm, from about 10 ppm to about 50 ppm, from about 10 ppm to about 40 ppm, from about 10 ppm to about 30 ppm, from about 20 ppm to about 60 ppm, from about 20 ppm to about 50 ppm, from about 20 ppm to about 40 ppm, or from about 20 ppm to about 30 ppm. In some embodiments, the fouling control composition or polyhydroxy multi-ionic compounds may be added to the water to an amount ranging from about 100 ppm to about 1000 ppm, from about 125 ppm to about 1000 ppm, from about 250 ppm to about 1000 ppm, or from about 500 ppm to about 1000 ppm in the treated water system.

The fouling control composition or polyhydroxy multi-ionic compounds can be used for fouling control in oil and gas applications such as by treating a gas or liquid stream with an effective amount of the compound or composition as described herein. The compounds and compositions can be used in any industry where it is desirable to prevent microbial or biofilm growth at a surface.

The fouling control composition or polyhydroxy multi-ionic compounds can be used in a condensate/oil systems/gas system, or any combination thereof. For example, the fouling control composition or polyhydroxy multi-ionic compounds can be used in fouling control on heat exchanger surfaces. The fouling control composition or polyhydroxy multi-ionic compounds can be applied to a gas or liquid produced, or used in the production, transportation, storage, and/or separation of crude oil or natural gas. The fouling control composition or polyhydroxy multi-ionic compounds can be applied to a gas stream used or produced in a coal-fired process, such as a coal-fired power plant.

The fouling control composition or polyhydroxy multi-ionic compounds can be applied to a gas or liquid produced or used in a waste-water process, a farm, a slaughter house, a land-fill, a municipality waste-water plant, a coking coal process, or a biofuel process.

A fluid to which the fouling control composition or polyhydroxy multi-ionic compounds can be introduced can be an aqueous medium. The aqueous medium can comprise water, gas, and optionally liquid hydrocarbon. A fluid to which the fouling control composition or polyhydroxy multi-ionic compounds can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid or gas can be a refined hydrocarbon product.

A fluid or gas treated with the fouling control composition or polyhydroxy multi-ionic compounds can be at any selected temperature, such as ambient temperature or an elevated temperature. The fluid (e.g., liquid hydrocarbon) or gas can be at a temperature of from about 40° C. to about 250° C. The fluid or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The fouling control composition or polyhydroxy multi-ionic compounds can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the fouling control composition or polyhydroxy multi-ionic compounds are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The fouling control composition or polyhydroxy multi-ionic compounds can be introduced into a fluid or gas of the water system by any appropriate method for ensuring dispersal through the fluid or gas. For examples, the fouling control composition or polyhydroxy multi-ionic compounds can be added to the hydrocarbon fluid before the hydrocarbon fluid contacts the surface. The fouling control composition or polyhydroxy multi-ionic compounds can be added at a point in a flow line upstream from the point at which fouling control is desired. The fouling control composition or polyhydroxy multi-ionic compounds can be injected using mechanical equipment such as chemical injection pumps, piping tees, injection fittings, atomizers, quills, and the like. The fouling control composition or polyhydroxy multi-ionic compounds can be pumped into an oil and/or gas pipeline using an umbilical line. A capillary injection system can be used to deliver the fouling control composition or polyhydroxy multi-ionic compounds to a selected fluid.

A fluid to which the fouling control composition or polyhydroxy multi-ionic compounds can be introduced can be an aqueous medium. The aqueous medium can comprise water, gas, and optionally liquid hydrocarbon. A fluid to the fouling control composition or polyhydroxy multi-ionic compounds can be introduced can be a liquid hydrocarbon.

The fouling control composition or polyhydroxy multi-ionic compounds can be introduced into a liquid and a mixture of several liquids, a liquid and gas, liquid, solid, and gas. The fouling control composition or polyhydroxy multi-ionic compounds can be injected into a gas stream as an aqueous or non-aqueous solution, mixture, or slurry. The fluid or gas can be passed through an absorption tower comprising the fouling control composition or polyhydroxy multi-ionic compounds.

The fouling control composition or polyhydroxy multi-ionic compounds can be applied to a fluid or gas to provide any selected concentration. In practice, the fouling control composition or polyhydroxy multi-ionic compounds are typically added to a flow line to provide an effective treating dose of the fouling control composition or polyhydroxy multi-ionic compounds from about 0.01 to about 5,000 ppm. The fouling control composition or polyhydroxy multi-ionic compounds can be applied to a fluid or gas to provide an active concentration of about 1 parts per million (ppm) to about 1,000,000 ppm, about 1 parts per million (ppm) to about 100,000 ppm, or from about 10 ppm to about 75,000 ppm. The polyhydroxy multi-ionic compounds can be applied to a fluid to provide an actives concentration of from about 100 ppm to about 10,000 ppm, from about 200 ppm to about 8,000 ppm, or from about 500 ppm to about 6,000 ppm. The actives concentration means the concentration of fouling control composition or polyhydroxy multi-ionic compounds.

The fouling control composition or polyhydroxy multi-ionic compounds can be applied to a fluid or gas to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm. The polymer salts/compositions can be applied to a fluid or gas to provide an actives concentration of about 0.125 ppm, about 0.25 ppm, about 0.625 ppm, about 1 ppm, about 1.25 ppm, about 2.5 ppm, about 5 ppm, about 10 ppm, or about 20 ppm in the treated fluid, gas, or water system. Each water system can have its own dose level requirements, and the effective dose level of the fouling control composition or polyhydroxy multi-ionic compounds to sufficiently reduce the rate of microbial or biofilm growth can vary with the water system in which it is used.

The fouling control composition or polyhydroxy multi-ionic compounds can be applied continuously, in batch, or a combination thereof. The fouling control composition or polyhydroxy multi-ionic compounds dosing can be continuous. The fouling control composition or polyhydroxy multi-ionic compounds dosing can be intermittent (e.g., batch treatment) or can be continuous/maintained and/or intermittent.

Dosage rates for continuous treatments typically range from about 10 to about 500 ppm, or from about 10 ppm to about 200 ppm. Dosage rates for batch treatments typically range from about 10 ppm to about 400,000 ppm, or from about 10 ppm to about 20,000 ppm. The fouling control composition or polyhydroxy multi-ionic compounds can be applied as a pill to a pipeline, providing a high dose (e.g., 20,000 ppm) of the composition.

The flow rate of a flow line in which the fouling control composition or polyhydroxy multi-ionic compounds is used can be between about 0.1 feet per second and about 100 feet per second, or between about 0.1 feet per second and about 50 feet per second. The fouling control composition or polyhydroxy multi-ionic compounds can also be formulated with water to facilitate addition to the flow line.

The surface can be a part of a wellbore or equipment used in the production, transportation, storage, and/or separation of a fluid such as crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The equipment can comprise a pipeline, a storage vessel, downhole injection tubing, a flow line, or an injection line.

The fouling control composition or polyhydroxy multi-ionic compounds are useful for corrosion inhibition of containers, processing facilities, or equipment in the food service or food processing industries. The fouling control composition or polyhydroxy multi-ionic compounds have particular value for use on food packaging materials and equipment, and especially for cold or hot aseptic packaging. Examples of process facilities in which the fouling control composition or polyhydroxy multi-ionic compounds can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The fouling control composition or polyhydroxy multi-ionic compounds can be used to inhibit corrosion in tanks, lines, pumps, and other equipment used for the manufacture and storage of soft drink materials, and also used in the bottling or containers for the beverages.

The fouling control composition or polyhydroxy multi-ionic compounds can also be used on or in other industrial equipment and in other industrial process streams such as heaters, cooling towers, boilers, retort waters, rinse waters, aseptic packaging wash waters, and the like. The fouling control composition or polyhydroxy multi-ionic compounds can be used to treat surfaces in recreational waters such as in pools, spas, recreational flumes and water slides, fountains, and the like.

The fouling control composition or polyhydroxy multi-ionic compounds can be used to treat surfaces contacted with cleaners in surfaces found in janitorial and/or housekeeping applications, food processing equipment and/or plant applications, and in laundry applications. For example, washers, such as tunnel washers for washing textiles, can be treated according to methods disclosed herein.

The fouling control composition or polyhydroxy multi-ionic compounds can be used or applied in combination with low temperature dish and/or ware wash sanitizing final rinse, toilet bowl cleaners, and laundry bleaches. The fouling control composition or polyhydroxy multi-ionic compounds can be used to treat metal surfaces, such as ware, cleaned and/or sanitized with corrosive sources.

The fouling control composition or polyhydroxy multi-ionic compounds can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The fouling control composition or polyhydroxy multi-ionic compounds can be dispensed by immersing either intermittently or continuously in the water, fluid, or gas of the water system. The fouling control composition or polyhydroxy multi-ionic compounds can then dissolve, for example, at a controlled or predetermined rate. The rate can be effective to maintain a concentration of the dissolved compounds or compositions that are effective for use according to the methods disclosed herein.

The fouling control composition disclosed herein can comprise from about 10 to about 90 wt-% of the carrier, biocide, corrosion inhibitor, additional fouling control composition agent, a combination thereof and from about 10 wt-% to about 90 wt-% of one or more polyhydroxy multi-ionic compounds; from about 20 wt-% to about 80 wt-% of the carrier, biocide, corrosion inhibitor, additional fouling control composition agent, a combination thereof and from about 10 wt-% to about 80 wt-% of one or more polyhydroxy multi-ionic compounds, from about 30 wt-% to about 70 wt-% of the carrier, biocide, corrosion inhibitor, additional fouling control composition agent, or a combination thereof and from about 30 wt-% to about 70 wt-% of one or more polyhydroxy multi-ionic compounds, or from about 40 wt-% to about 60 wt-% of the carrier, biocide, corrosion inhibitor, additional fouling control composition agent, or a combination thereof and from about 70 wt-% to about 84 wt. % of one or more polyhydroxy multi-ionic compounds.

Emulsion Inverters

In an embodiment, the polyhydroxy multi-ionic compounds can be used as emulsion inverters or combined with emulsion inverter compositions including one or more additional emulsion inverters composition agents. Also disclosed herein are methods of inverting an emulsion of water and oil comprising introducing an effective amount of an emulsion inverter composition into contact with the emulsion to destabilize the emulsion, wherein the emulsion inverter composition comprises a polyhydroxy multi-ionic compound as disclosed herein.

Rheology Modifiers

In an embodiment, the polyhydroxy multi-ionic compounds can be used as rheology modifiers. Also disclosed herein are methods of modifying viscosity of a composition comprising introducing an effective amount of a rheology modifier composition into contact with a composition or liquid component, wherein the rheology modifier composition comprises a polyhydroxy multi-ionic compound as disclosed herein.

Viscosity Reducer

In an embodiment, the polyhydroxy multi-ionic compounds can be used as viscosity reducers. Also disclosed herein are methods of reducing viscosity of a composition comprising introducing an effective amount of a viscosity reducer composition into contact with a composition or liquid component, wherein the viscosity reducer composition comprises a polyhydroxy multi-ionic compound as disclosed herein.

Drag Reducer

In an embodiment, the polyhydroxy multi-ionic compounds can be used as drag reducers. Also disclosed herein are methods of reducing drag of a fluid or composition comprising introducing an effective amount of a drag reducer composition into contact with a fluid or composition, wherein the drag reducer composition comprises a polyhydroxy multi-ionic compound as disclosed herein.

The present disclosure is further defined by the following numbered paragraphs:

A polyhydroxy multi-ionic compound having the structure of formula V or VII:

(V)

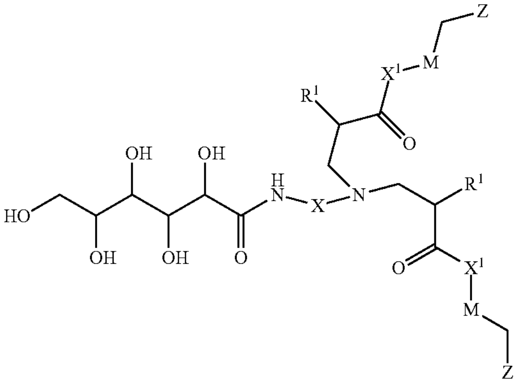

or

-continued (VII)

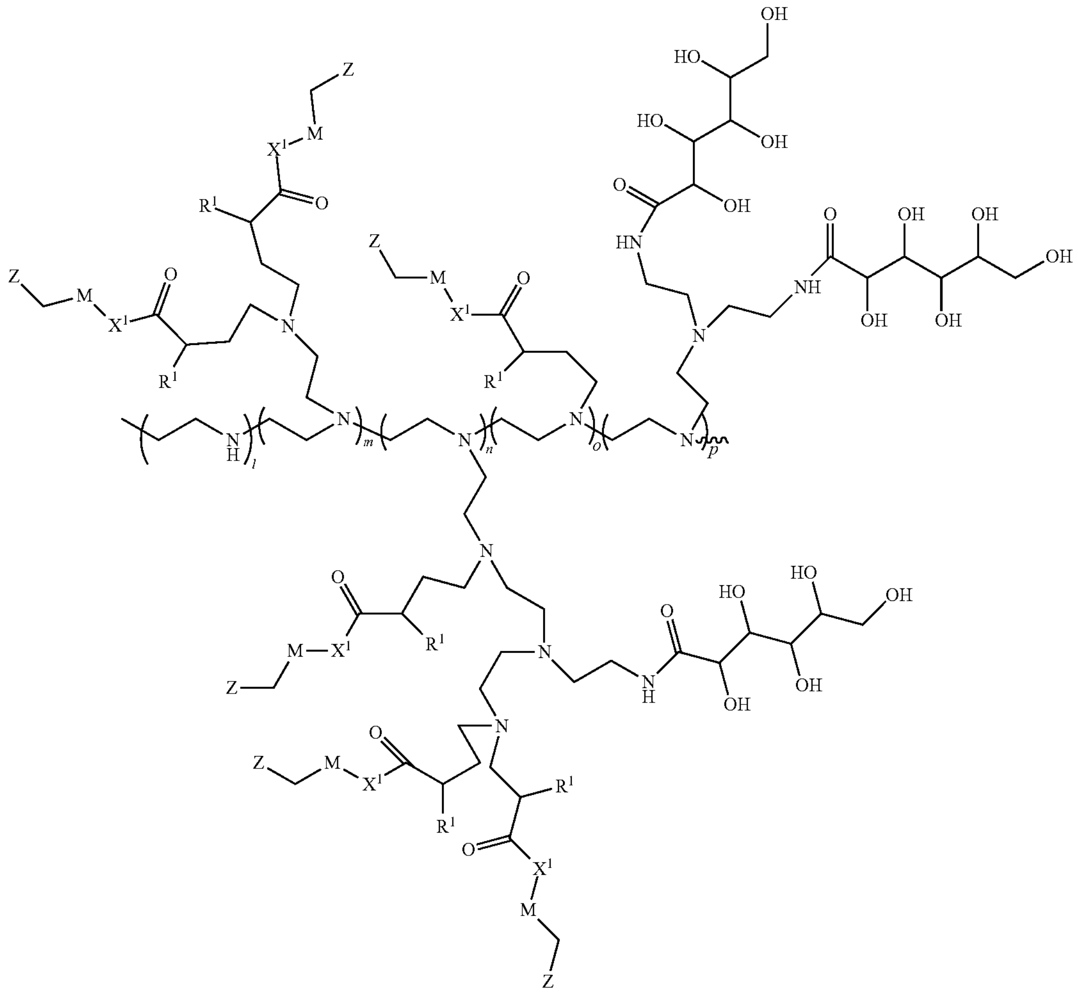

wherein.

l, m, n, o, and p are independently an integer of 0-1000, and wherein at least one of l, m, n, o, and/or p is an integer of 1-1000;

X is $—(CH_2)_{m1}—$, $—(Ar)—$, $—(CH_2Ar)_{n1}—$, $—((CH_2)_{o1}Ar(CH_2)_{o1})_{p1}—$, $—((CH_2)_qNH(CH_2)_q)_r—$, or $—(CH_2NDCH_2)_s—$, wherein D is H,

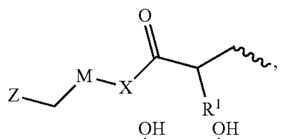

or

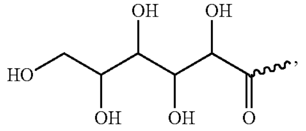

wherein $m_1$, $n_1$, $o_1$, and q are independently an integer from 0 to 10 and $p_1$, r, and s are independently an integer from 1 to 100;

$X^1$ is NH or O;

$R^1$ is H, $CH_3$, or an unsubstituted, linear or branched C2-C10 alkyl group;

M is absent or an unsubstituted, linear C1-C30 alkylene group;

Z is $—NR^3R^4R^5(+)$ $Y(-)$, —COOH, $—SO_3H$, $—PO_3H$, or a salt thereof; and $R^3$, $R^4$, and $R^5$ are independently C1-C10 alkyl group or benzyl group.

A polyhydroxy multi-ionic compound comprising: a reaction product obtained by either: (a) reacting a sugar lactone with a polyamine to form a sugar amide intermediate through amidation; and thereafter undergoing an aza-Michael addition reaction between the sugar amide intermediate and a cationic/anionic monomer to form the polyhydroxy multi-ionic compound of paragraph 1; or (b) simultaneously reacting a polyamine with a sugar lactone and a cationic/anionic monomer to form the polyhydroxy multi-ionic compound of paragraph 1.

The compound of paragraph 2, wherein the sugar lactone is selected from the group consisting of 1,5-D-gluconolactone ($C_6H_{10}O_6$), 1,4-D-galactonolactone, D-mannono-1,4-lactone, ascorbic acid, lactide, d-lactone, d-caprolactone, ε-caprolactone, g-butyrolactone, gulonic acid γ-lactone, b-propiolactone, coumarin, and whiskey lactone.

The compound of paragraph 3, wherein the sugar lactone is 1,5-D-gluconolactone.

The compound of any one of paragraphs 2-4, wherein the polyamine has the general formula $H_2N—X—NH_2$, wherein X is $—(CH_2)_{m1}—$, $—(Ar)—$, $—(CH_2Ar)_{n1}—$, $—((CH_2)_{o1}Ar(CH_2)_{o1})_{p1}$, $—((CH_2)_qNH(CH_2)_q)_r—$, or $—(CH_2NDCH_2)_s—$ wherein D is H,

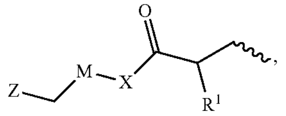
, or

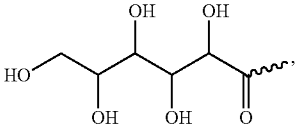

wherein $m_1$, $n_1$, $o_1$, and q are independently an integer from 0 to 10 and $p_1$, r, and s are independently an integer from 1 to 100.

The compound of paragraph 5, wherein the polyamine is a branched, linear, or dendrimer polyethyleneimine.

The compound of paragraph 6, wherein the polyethyleneimine has average molecular weight ($M_w$) between about 100-2,000,000 and/or is selected from the group consisting of diethylenetriamine, triethylenetetraamine, tetraethylenepentamine, pentaethylenehexamine, hexaethyleneheptamine, polyethyleneimines, tris(2-Aminoethyl)amine, ethyleneamine E-100, and mixtures thereof.

The compound of any one of paragraphs 2-4, wherein the molar ratio of the sugar lactone to the polyamine per amine group is at least about 1:1, at least about 2:1, at least about 3:1, at least about 4:1, or greater.

The compound of any one of paragraphs 2-8, wherein the cationic/anionic monomer has the formula (IV)

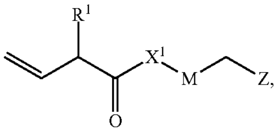

wherein $X^1$ is NH or O; $R^1$ is H, $CH_3$, or an unsubstituted, linear or branched C2-C10 alkyl group; M is absent or an unsubstituted, linear C1-C30 alkylene group; Z is $—NR^3R^4R^5(+)\ Y(-)$, —COOH, $—SO_3H$, $—PO_3H$, or a salt thereof, and $R^3$, $R^4$, and $R^5$ are independently C1-C10 alkyl group or benzyl group.

The compound of paragraph 9, wherein the cationic monomer is selected from the group consisting of (3-Acrylamidopropyl)trimethylammonium chloride (APTAC), 2-Acrylamido-2-methyl-1-propanesulfonic acid sodium salt (NaAMPS), [3-(Methacryloylamino)propyl]trimethylammonium chloride (MAPTAC), 2-(methacryloyloxy)-N,N,N-trimethylethanaminium chloride (DMAEMA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEMA-MSQ), and 2-(acryloyloxy)-N,N,N-trimethylethanaminium chloride (DMAEA-MCQ).

The compound of paragraph 9, wherein the anionic monomer is selected from the group consisting of acrylic acid, methacrylic acid, itaconic acid, maleic acid, vinylsulfonic acid, vinylphosphonic acid, and 3-(allyloxy)-2-hydroxypropane-1-sulfonate.

The compound of any one of paragraphs 2-11, wherein the reaction is conducted in the presence of a solvent.

The compound of any one of paragraphs 2-12, wherein the reaction is conducted at a temperature of at least about 0° C. to about 200° C.

The compound of any one of paragraphs 2-13, wherein the reaction is conducted at atmospheric pressure.

The compound of any one of paragraphs 2-14, wherein the reaction has a yield of at least about 90%, at least about 95%, or at least about 98%.

A method of synthesizing a polyhydroxy multi-ionic compound comprising: (a) reacting a sugar lactone with a polyamine to form a sugar amide intermediate through amidation; and thereafter undergoing an aza-Michael addition reaction between the sugar amide intermediate and a cationic/anionic monomer to form the polyhydroxy multi-ionic compound of paragraph 1; or (b) simultaneously reacting a polyamine with a sugar lactone and a cationic/anionic monomer to form the polyhydroxy multi-ionic compound of paragraph 1.

The method of paragraph 16, wherein the sugar lactone is selected from the group consisting of 1,5-D-gluconolactone ($C_6H_{10}O_6$), 1,4-D-galactonolactone, D-mannono-1,4-lactone, ascorbic acid, lactide, d-lactone, d-caprolactone, ε-caprolactone, g-butyrolactone, gulonic acid γ-lactone, b-propiolactone, coumarin, and whiskey lactone, and wherein the polyamine has the general formula $H_2N—X—NH_2$, wherein X is $—(CH_2)_{m1}—$, $—(Ar)—$, $—(CH_2Ar)_{n1}—$, $—((CH_2)_{o1}Ar(CH_2)_{o1})_{p1}—$, $—((CH_2)_qNH(CH_2)_q)_r—$, or $—(CH_2NDCH_2)_s—$ wherein D is H,

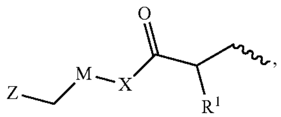
, or

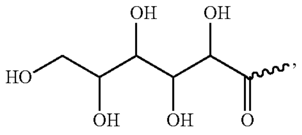

wherein $m_1$, $n_1$, $o_1$, and q are independently an integer from 0 to 10 and $p_1$, r, and s are independently an integer from 1 to 100.

The method of paragraph 17, wherein the polyamine is a branched, linear, or dendrimer polyethyleneimine, and wherein the polyethyleneimine has average molecular weight ($M_w$) between about 100-2,000,000, and/or is selected from the group consisting of diethylenetriamine, triethylenetetraamine, tetraethylenepentamine, pentaethylenehexamine, hexaethyleneheptamine, polyethyleneimines, tris(2-Aminoethyl)amine, ethyleneamine E-100, and mixtures thereof.

The method of any one of paragraphs 16-18, wherein the molar ratio of the sugar lactone to the polyamine per amine group is at least about 1:1, at least about 2:1, at least about 3:1, at least about 4:1, or greater.

The method of any one of paragraphs 16-19, wherein the cationic/anionic monomer has the formula (IV)

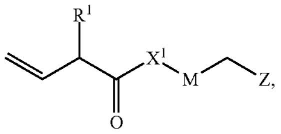

wherein $X^1$ is NH or O; $R^1$ is H, $CH_3$, or an unsubstituted, linear or branched C2-C10 alkyl group; M is absent or an unsubstituted, linear C1-C30 alkylene group; Z is $—NR^3R^4R^5(+)\ Y(-)$, —COOH, $—SO_3H$, $—PO_3H$, or a salt thereof; and $R^3$, $R^4$, and $R^5$ are independently C1-C10 alkyl group or benzyl group.

The method of paragraph 20, wherein the cationic monomer is selected from the group consisting of (3-Acrylamidopropyl)trimethylammonium chloride (APTAC), 2-Acrylamido-2-methyl-1-propanesulfonic acid sodium salt (NaAMPS), [3-(Methacryloylamino)propyl]trimethylammonium chloride (MAPTAC), 2-(methacryloyloxy)-N,N,N-trimethylethanaminium chloride (DMAEMA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEMA-MSQ), and 2-(acryloyloxy)-N,N,N-trimethylethanaminium chloride (DMAEA-MCQ), or wherein the anionic monomer is selected from the group consisting of acrylic acid, methacrylic acid, itaconic acid, maleic acid, vinylsulfonic acid, vinylphosphonic acid, and 3-(allyloxy)-2-hydroxypropane-1-sulfonate.

The method of any one of paragraphs 16-21, wherein the reaction is conducted in the presence of a solvent.

The method of any one of paragraphs 16-22, wherein the reaction is conducted at a temperature of at least about 0° C. to about 200° C.

The method of any one of paragraphs 16-23, wherein the reaction is conducted at atmospheric pressure.

The method of any one of paragraphs 16-24, wherein the reaction has a yield of at least about 90%, at least about 95%, or at least about 98%.

A method of breaking an emulsion of water and oil comprising introducing an effective amount of an emulsion breaker composition into contact with the emulsion to destabilize the emulsion, wherein the emulsion breaker composition comprises a polyhydroxy multi-ionic compound of any one of paragraphs 1 to 15.

The method of paragraph 26, wherein the emulsion breaker composition further comprises additional reverse emulsion breaker composition agent(s).

The method of paragraph 27, wherein the additional reverse emulsion breaker composition agent(s) comprises acid, carrier, dispersant, diluent, biocide, inorganic salt, organic salt, emulsifier, additional reverse emulsion breaker, corrosion inhibitor, antioxidant, polymer degradation prevention agent, permeability modifier, foaming agent, antifoaming agent, fracturing proppant, glass particulate, sand, fracture proppant/sand control agent, scavenger for $H_2S$, $CO_2$, and/or $O_2$, gelling agent, lubricant, and friction reducing agent, salt, or mixtures thereof.

The method of paragraph 28, wherein the additional reverse emulsion breaker composition agent(s) comprises a diluent, a corrosion inhibitor, an asphaltene inhibitor, an emulsion breaker, a gas hydrate inhibitor, and a biocide.

The method of any one of paragraphs 26-29, wherein the emulsion breaker composition comprises from about 1 wt-% to about 10 wt-% of an emulsion breaker.

The method of any one of paragraphs 26-30, wherein the emulsion breaker composition further comprises water.

The method of any one of paragraphs 26-31, wherein the emulsion breaker composition comprises from about 0.1 wt-% to about 20 wt-% of the polyhydroxy multi-ionic compound and from about 0 wt-% to about 75 wt-% of water.

The method of any one of paragraphs 26-32, wherein the emulsion breaker composition is used to break an emulsion in a produced fluid in oil and gas applications.

The method of paragraph 33, wherein the produced fluid is an aqueous medium comprising water, gas, oil, and optionally liquid hydrocarbon.

The method of any one of paragraphs 33-34, wherein the produced fluid is at a temperature from about −50° C. to about 300° C.

The method of any one of paragraphs 26-35, wherein the emulsion breaker composition is dispensed intermittently in a produced fluid.

The method of any one of paragraphs 26-35, wherein the emulsion breaker composition is dispensed continuously in a produced fluid.

The method of any one of paragraphs 26-37, wherein an effective amount of an emulsion breaker composition into contact with the emulsion is from about 0.01 ppm to about 5,000 ppm.

The method of any one of paragraphs 26-36, wherein contacting the emulsion breaker composition to the emulsion provides an active concentration of the emulsion breaker composition from about 1 ppm to about 1,000,000 ppm.

A method of clarifying a water source comprising introducing an effective amount of a water clarification composition into contact with the water source, wherein the water clarification composition comprises a polyhydroxy multi-ionic compound of any one of paragraphs 1 to 15.

The method of paragraph 40, wherein the water source is an industrial water system, a cooling water system, a waste water source, a condensate system, an oil system, a gas system, the water of a heat exchanger, a gas stream, or any combination thereof.

The method of any one of paragraphs 40-41, wherein introducing the water clarification composition contacts the water source via the water of the water source.

The method of any one of paragraphs 40-42, wherein the water clarification composition is diluted with water by a factor of about 0.5 to about 1,000,000.

The method of any one of paragraphs 40-43, wherein the effective amount of the water clarification composition is from about 1 ppm to about 1,000 ppm.

The method of any one of paragraphs 40-44, wherein the water source comprises an aqueous medium that is contacted by the water clarification composition.

The method of paragraph 45, wherein the aqueous medium is water, gas, and optionally liquid hydrocarbon.

The method of paragraphs 45-46, wherein the aqueous medium is at a temperature of about 0° C. to about 300° C.

The method of any one of paragraphs 40-47, wherein contacting the water clarification composition to the water source provides an active concentration of the emulsion breaker composition from about 1 ppm to about 1,000,000 ppm.

The method of any one of paragraphs 40-48, wherein the water clarification composition is dispensed intermittently in the water source.

The method of any one of paragraphs 40-48, wherein the water clarification composition is dispensed continuously in the water source.

A method of stabilizing swellable clays and/or reducing formation of sludge in a subterranean formation comprising introducing an effective amount of a clay treatment composition into a subterranean formation with a fluid, wherein the clay treatment composition comprises a polyhydroxy multi-ionic compound of any one of paragraphs 1 to 15.

The method of paragraph 51, wherein the clay treatment composition has a concentration of about 1 ppm to about 7,000 ppm.

The method of any one of paragraphs 51-52, wherein the fluid is water, oil, and optionally liquid hydrocarbon.

The method of any one of paragraphs 51-53, wherein the fluid is at a temperature of about 0° C. to about 300° C.

The method of any one of paragraphs 51-54, wherein the clay treatment composition is dispensed intermittently in the water source.

The method of any one of paragraphs 51-54, wherein the clay treatment composition is dispensed continuously in the water source.

The method of any one of paragraphs 51-56, wherein the clay treatment composition comprises additional clay treatment composition agent(s).

The method of paragraph 57, wherein the clay treatment composition comprises from about 10 wt-% to about 90 wt-% of the additional clay treatment composition agent(s).

A method of inverting an emulsion of water and oil comprising introducing an effective amount of an emulsion inverter composition into contact with the emulsion to destabilize the emulsion, wherein the emulsion inverter composition comprises a polyhydroxy multi-ionic compound of any one of paragraphs 1 to 15.

The method of paragraph 59, wherein the emulsion inverter composition further comprises additional emulsion inverter composition agent(s).

The method of paragraph 60, wherein the additional emulsion inverter composition agent(s) comprises acid, carrier, dispersant, diluent, biocide, inorganic salt, organic salt, emulsifier, additional reverse emulsion breaker, corrosion inhibitor, antioxidant, polymer degradation prevention agent, permeability modifier, foaming agent, antifoaming agent, fracturing proppant, glass particulate, sand, fracture proppant/sand control agent, scavenger for $H_2S$, $CO_2$, and/or $O_2$, gelling agent, lubricant, and friction reducing agent, salt, or mixtures thereof.

The method of any one of paragraphs 59-61, wherein the emulsion inverter composition comprises from about 1 wt-% to about 10 wt-% of an emulsion breaker.

The method of any one of paragraphs 59-62, wherein the emulsion inverter composition further comprises water.

The method of any one of paragraphs 59-63, wherein the emulsion inverter composition comprises from about 0.1 wt-% to about 20 wt-% of the polyhydroxy multi-ionic compound and from about 0 wt-% to about 75 wt-% of water.

The method of any one of paragraphs 59-64, wherein the emulsion inverter composition is used to destabilize an emulsion in a produced fluid in oil and gas applications.

The method of paragraph 65, wherein the produced fluid is an aqueous medium comprising water, gas, oil, and optionally liquid hydrocarbon.

The method of any one of paragraphs 65-66, wherein the produced fluid is at a temperature from about −50° C. to about 300° C.

The method of any one of paragraphs 59-67, wherein the emulsion inverter composition is dispensed intermittently in a produced fluid.

The method of any one of paragraphs 59-68, wherein the emulsion inverter composition is dispensed continuously in a produced fluid.

The method of any one of paragraphs 59-69, wherein the effective amount of an emulsion inverter composition into contact with the emulsion is from about 0.01 ppm to about 5,000 ppm.

A method of inhibiting bio-film comprising introducing an effective amount of a bio-film inhibitor composition, wherein the bio-film inhibitor composition comprises a polyhydroxy multi-ionic compound of any one of paragraphs 1 to 15.

The method of paragraph 71, wherein the bio-film inhibitor is added to a water source to inhibit bio-film.

The method of paragraph 72, wherein the water source is an industrial water system, a cooling water system, a waste water source, a condensate system, an oil system, a gas system, the water of a heat exchanger, a gas stream, or any combination thereof.

The method of any one of paragraphs 71-73, wherein the bio-film inhibitor composition is diluted with water by a factor of about 0.5 to about 1,000,000.

The method of any one of paragraphs 71-74, wherein the effective amount of the bio-film inhibitor composition is from about 1 ppm to about 1,000 ppm.

The method of any one of paragraphs 71-75, wherein the water source comprises an aqueous medium that is contacted by the bio-film inhibitor composition.

The method of paragraph 76, wherein the aqueous medium is water, gas, and optionally liquid hydrocarbon.

The method of paragraphs 76-77, wherein the aqueous medium is at a temperature of about 0° C. to about 300° C.

The method of any one of paragraphs 71-78, wherein contacting the bio-film inhibitor composition to the water source provides an active concentration of the bio-film inhibitor composition from about 1 ppm to about 1,000,000 ppm.

The method of any one of paragraphs 72-79, wherein the bio-film inhibitor composition is dispensed intermittently in the water source.

The method of any one of paragraphs 72-80, wherein the bio-film inhibitor composition is dispensed continuously in the water source.

A method of reducing drag in a fluid comprising introducing an effective amount of a drag reducer composition comprising a polyhydroxy multi-ionic compound of any one of paragraphs 1 to 15.

The method of paragraph 82, wherein the drag reducer composition contacts a fluid to reduce drag.

The method of any one of paragraphs 82-83, wherein the drag reducer composition is diluted with water by a factor of about 0.5 to about 1,000,000.

The method of any one of paragraphs 82-84, wherein the effective amount of the drag reducer composition is from about 1 ppm to about 1,000 ppm.

The method of any one of paragraphs 82-85, wherein the fluid is water, gas, and optionally liquid hydrocarbon.

The method of paragraphs 82-86, wherein the fluid is at a temperature of about 0° C. to about 300° C.

The method of any one of paragraphs 82-87, wherein contacting the drag reducer composition to the fluid provides an active concentration of the drag reducer composition from about 1 ppm to about 1,000,000 ppm.

The method of any one of paragraphs 82-88, wherein the drag reducer composition is dispensed intermittently in the fluid.

The method of any one of paragraphs 82-88, wherein the drag reducer composition is dispensed continuously in the fluid.

A method of viscosity and/or rheology modification comprising introducing an effective amount of viscosity and/or rheology modifier composition, wherein the viscosity and/or rheology modifier composition comprises a polyhydroxy multi-ionic compound of any one of paragraphs 1 to 15.

The method of paragraph 91, wherein the viscosity and/or rheology modifier composition contacts a fluid to modify viscosity and/or rheology.

The method of any one of paragraphs 91-92, wherein the viscosity and/or rheology modifier composition is diluted with water by a factor of about 0.5 to about 1,000,000.

The method of any one of paragraphs 91-93, wherein the effective amount of the viscosity and/or rheology modifier composition is from about 1 ppm to about 1,000 ppm.

The method of any one of paragraphs 91-94, wherein the fluid is water, gas, and optionally liquid hydrocarbon.

The method of paragraphs 91-95, wherein the fluid is at a temperature of about 0° C. to about 300° C.

The method of any one of paragraphs 91-96, wherein contacting the viscosity and/or rheology modifier composition to the fluid provides an active concentration of the viscosity and/or rheology modifier composition from about 1 ppm to about 1,000,000 ppm.

The method of any one of paragraphs 91-97, wherein the viscosity and/or rheology modifier composition is dispensed intermittently in the fluid.

The method of any one of paragraphs 91-97, wherein the viscosity and/or rheology modifier composition is dispensed continuously in the fluid.

The method of any one of paragraphs 91-99, wherein an effective amount of the viscosity and/or rheology modifier composition is from about 0.01 ppm to about 5,000 ppm.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Figure 3A:
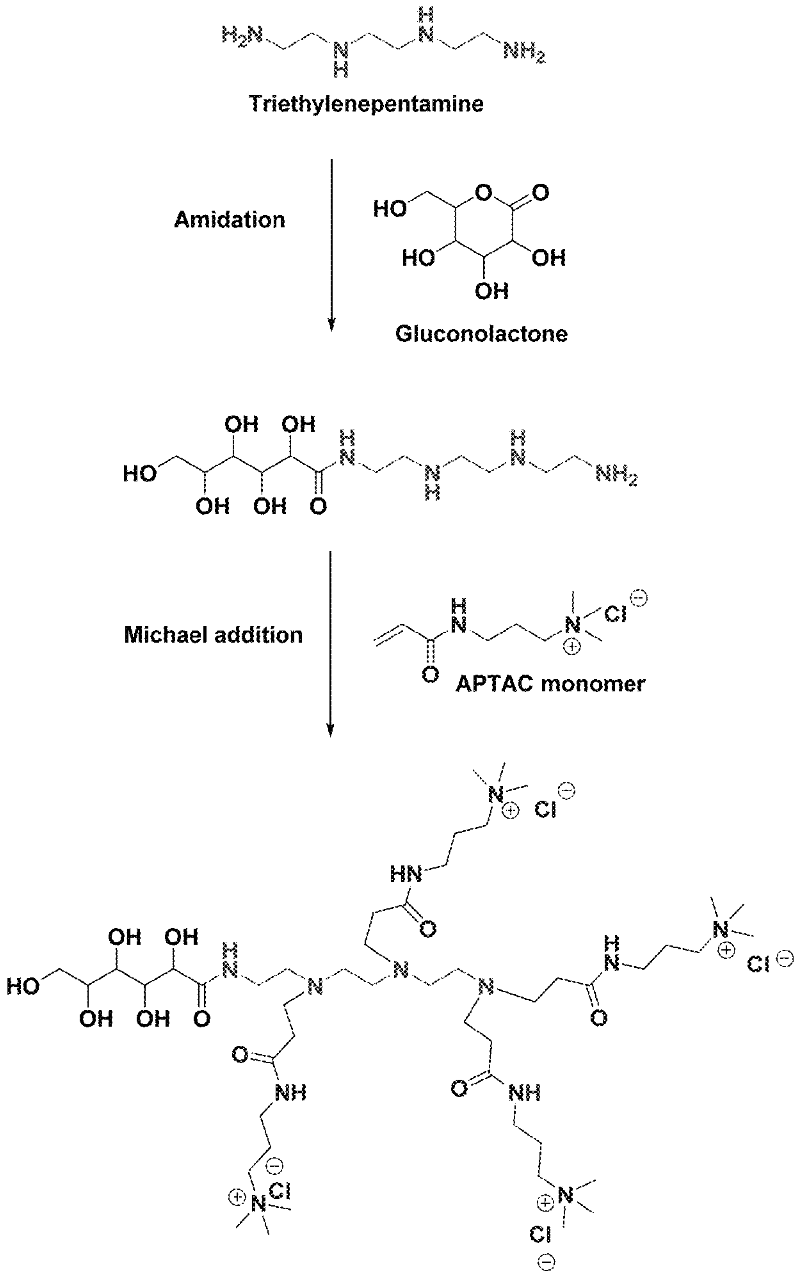
FIG. 3A shows an exemplary synthesis of polyhydroxy multi-ionic compounds.

Exemplary polyhydroxy multi-ionic compounds were synthesized. Generally, the synthesis described can be illustrated by FIG. 3A. The compounds were synthesized by equipping a 2 L reactor with a temperature probe, nitrogen inlet, condenser and magnetic stir bar. 1200 mL methanol and 178.14 g (1 mol) of d-gluconolactone were added to the 2 L reactor. The resulting slurry was then stirred for 15 minutes to obtain a clear solution. Next, 146.23 g (1 mol) of triethylenetetramine (TETA) was added to the reaction over the course of 30 minutes and the reaction was then stirred at 40° C. overnight. The solvent was then removed under vacuum to obtain the resulting mono-amide product (glucoonamide). 0.05 mol gluconamide was added to a stirred mixture of 0.25 mol of (3-acrylamidopropyl) trimethylammonium chloride (APTAC), 0.0005 mol of benzyltrimethylammonium hydroxide (an optional catalyst), and water at ambient temperature. Notably, the mixture is water soluble and able to react without the presence of a catalyst. This mixture was then stirred at 80° C. overnight or until the reaction was completed.

Example 2

Figure 3B:
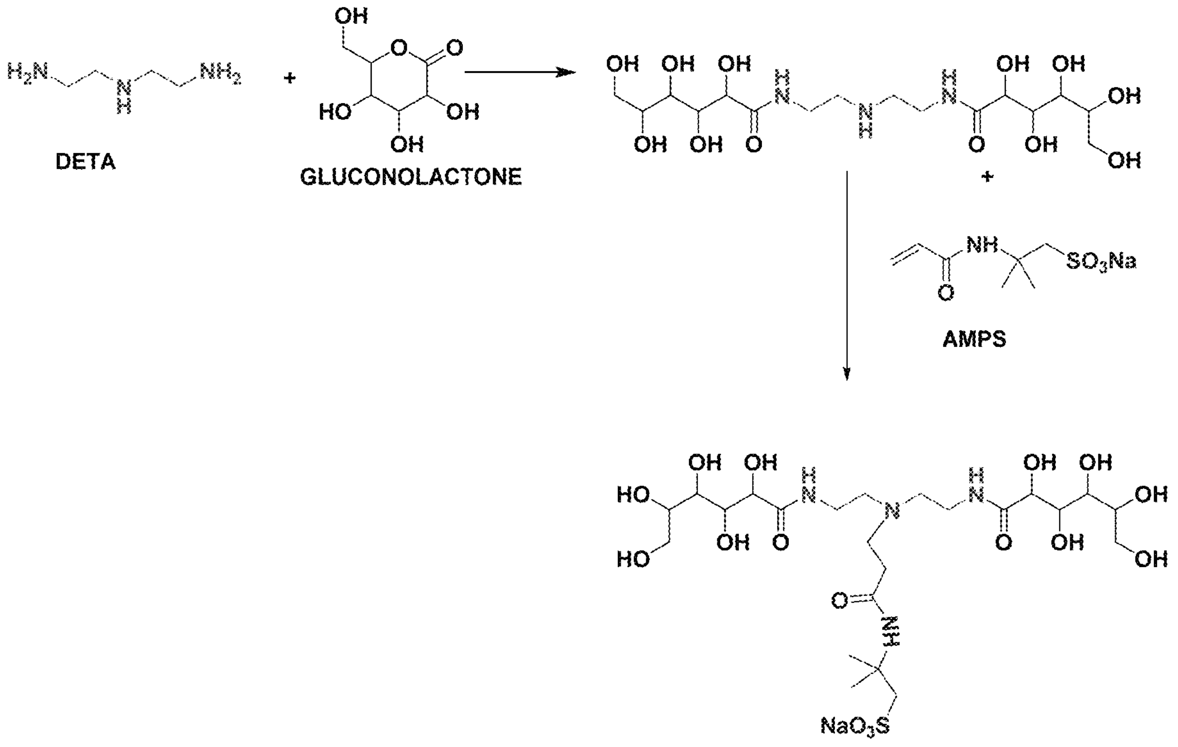
FIG. 3B shows an exemplary synthesis of polyhydroxy multi-ionic compounds.

The synthesis route of an additional exemplary polyhydroxy multi-ionic compound is illustrated in FIG. 3B. FIG. 3B shows the two-step reaction process of combining the sugar lactone 1,5-D-gluconolactone (gluconolactone) and the polyamine diethylenetriamine (DETA) for an amidation step to form the sugar amide bis(glucuronylaminoethyl) amine. Then 2-Acrylamido-2-methyl-1-propanesulfonic acid sodium salt (AMPS) is added as the ionic group to be used as the Michael acceptor to form the polyhydroxy multi-ionic compound shown.

Figure 3C:
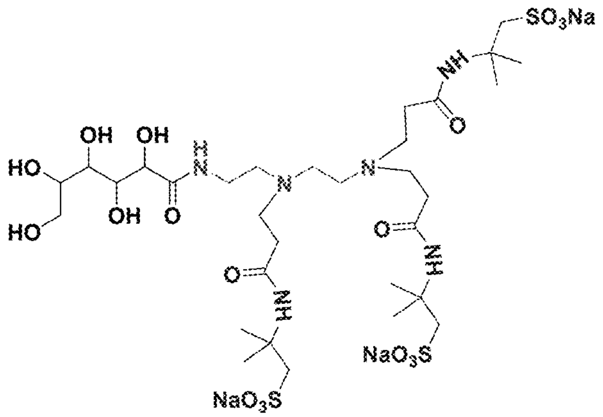
FIG. 3C shows an exemplary polyhydroxy multi-ionic compound.

The same two-step synthesis route as shown in FIG. 3B can form a the polyhydroxy multi-ionic compound shown in FIG. 3C when starting the synthesis with the polyamine triethylenetetramine (TETA) instead of diethylenetriamine (DETA) to have an additional amine groups to react with the lactone and the α,β-unsaturated carbonyl compound-based monomers so that no secondary amines remain.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. Any reference to accompanying drawings which form a part hereof, are shown, by way of illustration only. It is understood that other embodiments may be utilized and structural changes may be made without departing from the scope of the present disclosure. All publications discussed and/or referenced herein are incorporated herein in their entirety.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A polyhydroxy multi-ionic compound having the structure of formula (V) or (VII):

(V)

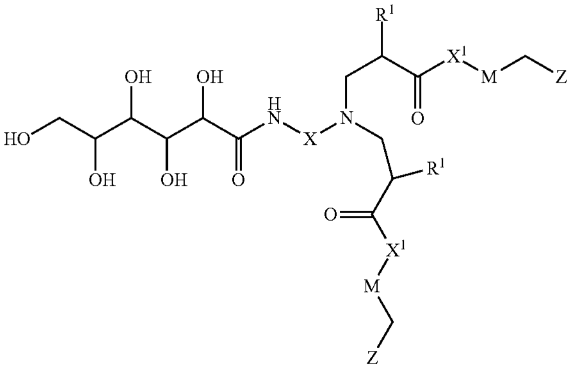

or (VII)

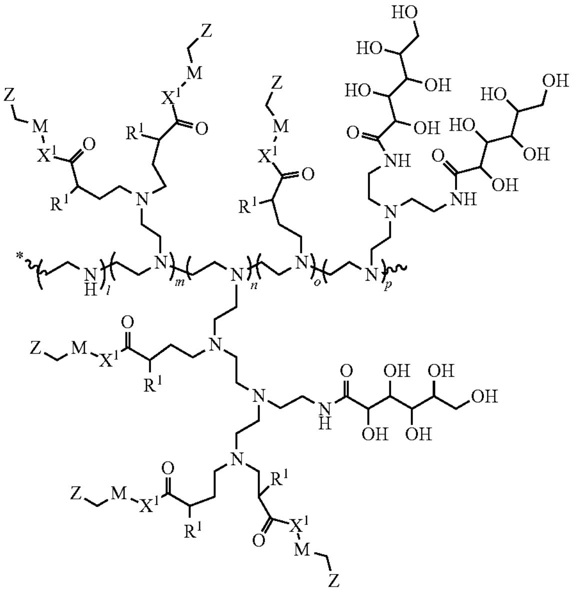

wherein:

l, m, n, o, and p are independently an integer of 0-1000, and wherein at least one of l, m, n, o, and/or p is an integer of 1-1000;

X is $—(CH_2)_{m1}—$, $—(Ar)—$, $—(CH_2Ar)_{n1}—$, $—((CH_2)_{o1}Ar(CH_2)_{o1})_{p1}—$, $—((CH_2)_q(NH(CH_2)_q)_r—$, or $—(CH_2NDCH_2)_s—$, wherein D is H,

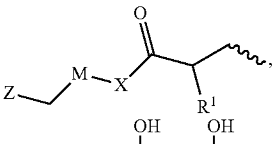

, or

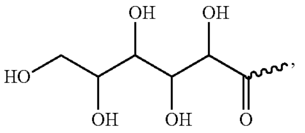

wherein $m_1$, $n_1$, $o_1$, and q are independently an integer from 0 to 10 and $p_1$, r, and s are independently an integer from 1 to 100;

$X^1$ is NH or O;

$R^1$ is H, $CH_3$, or an unsubstituted, linear or branched C2-C10 alkyl group;

M is absent or an unsubstituted, linear C1-C30 alkylene group;

Z is $—NR^3R^4R^5(+)\,Y(-)$, —COOH, $—SO_3H$, $—PO_3H_2$, or a salt thereof; and $R^3$, $R^4$ and $R^5$ are independently C1-C10 alkyl group or benzyl group.

2. A method of synthesizing a polyhydroxy multi-ionic compound comprising:

(a) reacting a sugar lactone with a polyamine to form a sugar amide intermediate through amidation; and thereafter undergoing an aza-Michael addition reaction between the sugar amide intermediate and a cationic/anionic monomer to form the polyhydroxy multi-ionic compound of claim 1; or (b) simultaneously reacting a polyamine with a sugar lactone and a cationic/anionic monomer to form the polyhydroxy multi-ionic compound of claim 1.

3. The method of claim 2, wherein the sugar lactone is selected from the group consisting of 1,5-D-gluconolactone ($C_6H_{10}O_6$), 1,4-D-galactonolactone, and D-mannono-1,4-lactone, and wherein the polyamine has the general formula $H_2N—X—NH_2$, wherein X is $—(CH_2)_{m1}—$, $((CH_2)_qNH(CH_2)_q)_r—$, or $—(CH_2NDCH_2)_s—$ wherein D is H,

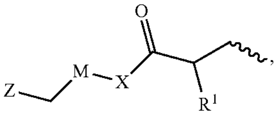

, or

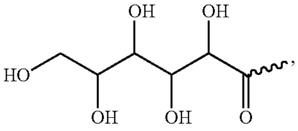

wherein $m_1$ and q are independently an integer from 0 to 10 and r and s are independently an integer from 1 to 100.

4. The method of claim 3, wherein the polyamine is a branched, linear, or dendrimer polyethyleneimine, and wherein the polyethyleneimine has average molecular weight ($M_w$) between about 100-2,000,000, and/or is selected from the group consisting of diethylenetriamine, triethylenetetraamine, and mixtures thereof.

5. The method of claim 2, wherein the molar ratio of the sugar lactone to the polyamine per amine group is at least about 1:1 or greater.

6. The method of claim 2, wherein the cationic/anionic monomer has the formula (IV)

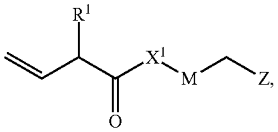

wherein $X^1$ is NH or O; $R^1$ is H, $CH_3$; M is absent or an unsubstituted, linear C1-C30 alkylene group; Z is $—NR^3R^4R^5(+)\,Y(-)$, $—SO_3H$, or a salt thereof; and $R^3$, $R^4$, and $R^5$ are independently C1-C10 alkyl group or benzyl group.

7. The method of claim 6, wherein the cationic monomer is selected from the group consisting of (3-Acrylamidopropyl)trimethylammonium chloride (APTAC) and 2-Acrylamido-2-methyl-1-propanesulfonic acid sodium salt (NaAMPS).

8. The method of claim 2, wherein the reaction is conducted in the presence of a solvent, wherein the reaction is conducted at a temperature of at least about 0° C. to about 200° C., and/or wherein the reaction is conducted at atmospheric pressure.

9. The method of claim 2, wherein the reaction has a yield of at least about 90%.

10. The compound of claim 1, wherein the compound has the structure of formula (V) wherein X is $-(CH_2)_{m1}-$, $-((CH_2)_qNH(CH_2)_q)_r-$, or $-(CH_2NDCH_2)_s-$;

wherein D is H,

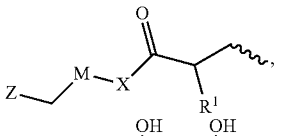

or

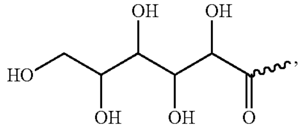

wherein $m_1$ and q are independently an integer from 0 to 10 and r and s are independently an integer from 1 to 100;

$X^1$ is NH or O;

$R^1$ is H, $CH_3$, or an unsubstituted, linear or branched C2-C10 alkyl group;

M is absent or an unsubstituted, linear C1-C30 alkylene group;

Z is $-NR^3R^4R^5(+)$ Y(−), —COOH, $-SO_3H$, $PO_3H_2$, or a salt thereof, and $R^3$, $R^4$ and $R^5$ are independently C1-C10 alkyl group or benzyl group.

11. The compound of claim 1, wherein the compound has the structure of formula (V) wherein X is $-(CH_2NDCH_2)_s-$; wherein D is (IV)

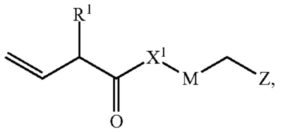

wherein s is independently an integer from 1 to 100;

$X^1$ is NH or O;

$R^1$ is H, $CH_3$, or an unsubstituted, linear or branched C2-C10 alkyl group;

M is absent or an unsubstituted, linear C1-C30 alkylene group;

Z is $-NR^3R^4R^5(+)$ Y(−), —COOH, $-SO_3H$, $PO_3H_2$, or a salt thereof; and $R^3$, $R^4$ and $R^5$ are independently C1-C10 alkyl group or benzyl group.

12. The compound of claim 11, wherein $X^1$ is NH.

13. The compound of claim 11, wherein $R^1$ is H or $CH_3$.

14. The compound of claim 11, wherein M is absent or an unsubstituted, linear C1-C3 alkylene group.

15. The compound of claim 11, wherein Z is $-NR^3R^4R^5$ (+) Y(−), $-SO_3H$, $PO_3H_2$, or a salt thereof; and $R^3$, $R^4$ and $R^5$ are independently C1-C10 alkyl group.

16. The compound of claim 1, wherein the compound has the structure of formula (V) wherein X is $-(CH_2NDCH_2)_s-$; wherein D is (IV)

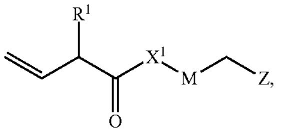

wherein s is 1; $X^1$ is NH; $R^1$ is H; M is an unsubstituted, linear C1-C3 alkylene group; and Z is $-SO_3H$, or a salt thereof.

17. The compound of claim 1, wherein the compound has the structure of formula (V) wherein X is $-(CH_2NDCH_2)_s-$; wherein D is (IV)

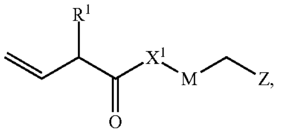

wherein s is 2; $X^1$ is NH; $R^1$ is H; M is absent; Z is $-NR^3R^4R^5(+)$ Y(−), or a salt thereof; and $R^3$, $R^4$ and $R^5$ are independently C1-C10 alkyl group or benzyl group.

18. The compound of claim 1, wherein the compound has the structure of formula (VII), wherein l, m, and n are 0 and wherein o and p are 1-1000; $X^1$ is NH; $R^1$ is H or $CH_3$; M is absent or an unsubstituted, linear C1-C3 alkylene group; and Z is $-SO_3H$, $-PO_3H_2$, or a salt thereof.

19. The compound of claim 1, wherein the compound has the structure of formula (VII), wherein l, m, and n are 0 and wherein o and p are 1-10; $X^1$ is NH; $R^1$ is H or $CH_3$; M is an unsubstituted, linear C1-C3 alkylene group; and Z is $-SO_3H$, $PO_3H_2$, or a salt thereof.

20. The compound of claim 18, wherein the compound has the structure of formula (VII), wherein l, m, and n are 0 and wherein o and p are 1; $X^1$ is NH; $R^1$ is H; M is an unsubstituted, linear C1-C3 alkylene group; and Z is $-SO_3H$ or a salt thereof.

* * * * *